United States Patent
Schuch

(10) Patent No.: US 10,851,401 B2
(45) Date of Patent: Dec. 1, 2020

(54) BROTH MICRODILUTION METHOD FOR EVALUATING AND DETERMINING MINIMAL INHIBITORY CONCENTRATION OF ANTIBACTERIAL POLYPEPTIDES

(71) Applicant: ContraFect Corporation, Yonkers, NY (US)

(72) Inventor: Raymond Schuch, Mountain Lakes, NJ (US)

(73) Assignee: CONTRAFECT CORPORATION, Yonkers, NY (US)

( * ) Notice: Subject to any disclaimer, the term of this patent is extended or adjusted under 35 U.S.C. 154(b) by 76 days.

(21) Appl. No.: 16/096,746

(22) PCT Filed: May 12, 2017

(86) PCT No.: PCT/US2017/032344
§ 371 (c)(1),
(2) Date: Oct. 26, 2018

(87) PCT Pub. No.: WO2017/197227
PCT Pub. Date: Nov. 16, 2017

(65) Prior Publication Data
US 2019/0106724 A1    Apr. 11, 2019

Related U.S. Application Data

(60) Provisional application No. 62/335,129, filed on May 12, 2016.

(51) Int. Cl.
*C12Q 1/18* (2006.01)
*C12Q 1/34* (2006.01)

(52) U.S. Cl.
CPC .............. *C12Q 1/18* (2013.01); *C12Q 1/34* (2013.01); *C12Y 302/01017* (2013.01)

(58) Field of Classification Search
CPC ..... C12Q 1/18; C12Q 1/34; C12Y 302/01017
See application file for complete search history.

(56) References Cited

U.S. PATENT DOCUMENTS

2015/0290299 A1   10/2015   Schuch et al.

FOREIGN PATENT DOCUMENTS

| EP | 2578597 A1 | 4/2013 | |
| WO | WO-2013170015 A1 * | 11/2013 | ......... A61K 31/4188 |

OTHER PUBLICATIONS

Anders et al. Amyloid-Related S UM Protein SAA From Three Animal Species: Comparison With Human SAA. The Journal of Immunology (1977), 118(1), 229-234. (Year: 1977).*

(Continued)

*Primary Examiner* — Sean C. Barron
(74) *Attorney, Agent, or Firm* — MH2 Technology Law Group LLP

(57) ABSTRACT

The present invention provides components, assays and methods for evaluating antibacterial effectiveness and determining minimal inhibitory concentration (MIC) of polypeptides, including lysin polypeptides, that kill bacteria. Modified broth microdilution components and methods are provided, including supplements to enable accurate MIC determination mimicking lysin polypeptide activity in human matrices including serum and blood.

16 Claims, 12 Drawing Sheets

Specification includes a Sequence Listing.

Problem

| Growth Medium | Freeze/Thaw | MIC$_{50}$ | MIC$_{90}$ | Range | Trailing | |
|---|---|---|---|---|---|---|
| 100% Human Serum | no | 0.5 | 1 | 0.125-2 | none | |
| MHB II | no | 32 | 64 | 2-128 | strong | } Trailing/Freezing |
| | yes | 128 | 256 | 32->256 | strong | |
| MHB II, 25% horse serum | no | 1 | 2 | 0.5-4 | none | } Freezing |
| | yes | 2 | 2 | 0.5-8 | none | |
| MHB II, 25% horse serum, 0.5 mM DTT | no | 0.5 | 1 | 0.25-2 | none | } NONE |
| | yes | 0.5 | 1 | 0.25-2 | none | |
| MHB II, 0.5 mM DTT | no | 128 | 128 | 8-256 | strong | } Trailing/Freezing |
| | yes | 128 | 256 | 64->256 | strong | |

(56) References Cited

OTHER PUBLICATIONS

J.B.Brooksby. The Serum Proteins of the Domestic Animals(Proc R Soc Med (1947), 40(5), 187-189. (Year: 1947).*
Farer et al. Thyroxine-Serum Protein Complexes in Various Animals. Endocrinology, vol. 70, Issue 5, May 1, 1962, pp. 686-696. (Year: 1962).*
D.H. Moore. Species difference in serum protein patterns. JBC (1945), 161, 21-32. (Year: 1945).*
Srivastava et al. Species differences in levonorgestrel binding to serum proteins of monkey, rabbit and rat blood. Exp Clin Endocrinol. Oct. 1984;84(2):218-22. (Year: 1984).*
Zaias et al. Reference Values for Serum Proteins of Common Laboratory Rodent Strains. Journal of the American Association for Laboratory Animal Science (2009), 48(4), 387-390. (Year: 2009).*
Horwitz, et al., "Bactericidal/permeability-increasing protein inhibits growth of a strain of acholeplasma laidlawii and L forms of the gram-positive bacteria *Staphylococcus aureus* and *Streptococcus pyogenes*", Antimicrob Agents Chemother., 1999, 43(9), pp. 2314-2316.
International Search Report for PCT/US2017/032344 dated Aug. 25, 2017.
Leuthner, et al., "Comparative activity of the new lipoglycopeptide telavancin in the presence and absence of serum against 50 glycopeptide non-susceptible staphylococci and three vancomycin-resistant *Staphylococcus aureus*", J. Antimicrob Chemother., 2006, 58(2), pp. 338-343.
Angioni, C.F., Extended European Search Report issued in corresponding European Patent Application No. 17796910.2 dated Nov. 13, 2019, 7 pages.
Scotti, R. et al., "Effect of protein on ramoplanin broth microdilution minimum inhibitory concentrations", Diagnostic Microbiology and Infectious Disease, Elsevier, vol. 17, No. 3, Oct. 1, 1993, pp. 209-211.
Raymond Schuch et al., "Combination Therapy With Lysin CF-301 and Antibiotic is Superior to Antibiotic Alone for Treating Methicillin-Resistant *Staphylococcus aureus*-Induced Murine Bacteremia", The Journal of Infectious Diseases 2014, vol. 209, No. 9, pp. 1469-1478.

* cited by examiner

FIGURE 2
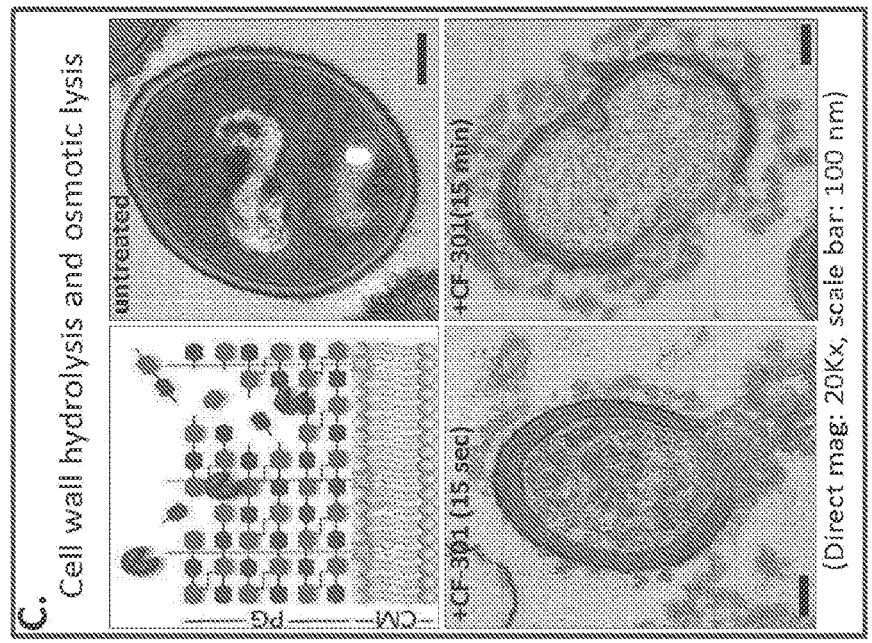
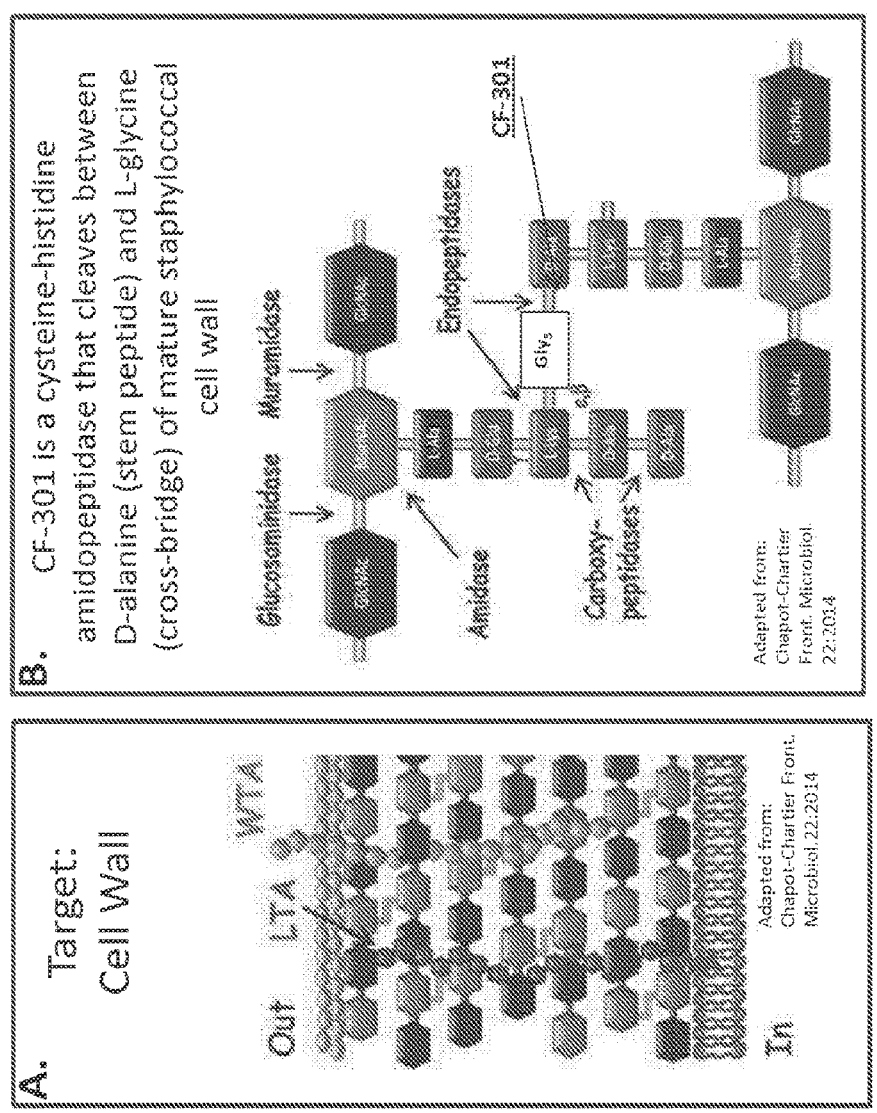

FIGURE 4

| Growth Medium | Freeze/Thaw | MIC$_{50}$ | MIC$_{90}$ | Range | Trailing | Problem |
|---|---|---|---|---|---|---|
| 100% Human Serum | no | 0.5 | 1 | 0.125-2 | none | |
| MHB II | no | 32 | 64 | 2-128 | strong | Trailing/Freezing |
| MHB II | yes | 128 | 256 | 32->256 | strong | |
| MHB II, 25% horse serum | no | 1 | 2 | 0.5-4 | none | Freezing |
| MHB II, 25% horse serum | yes | 2 | 2 | 0.5-8 | none | |
| MHB II, 25% horse serum, 0.5 mM DTT | no | 0.5 | 1 | 0.25-2 | none | NONE |
| | yes | 0.5 | 1 | 0.25-2 | none | |
| MHB II, 0.5 mM DTT | no | 128 | 128 | 8-256 | strong | Trailing/Freezing |
| | yes | 128 | 256 | 64->256 | strong | |

FIGURE 5

BMD analysis of *S. aureus* ATCC 29213 and *E. faecalis* ATCC 29212 on 5 consecutive days using 14 different sources of horse serum

| Horse serum source | Day 1 | | Day 2 | | Day 3 | | Day 4 | | Day 5 | |
|---|---|---|---|---|---|---|---|---|---|---|
| | S.aureus | E.faecalis | S.aureus | E.faecalis | S.aureus | E.faecalis | S.aureus | E.faecalis | S.aureus | E.faecalis |
| Sigma (summer 2015, mixed breed) | 0.5 | 32 | 0.5 | 32 | 0.5 | 32 | 0.5 | 32 | 0.5 | 32 |
| Mediatech (fall 2014, male, cold blood**) | 0.5 | 32 | 0.5 | 32 | 0.5 | 32 | 0.5 | 32 | 0.5 | 32 |
| Sigma (winter 2014, mixed breed) | 0.5 | 32 | 0.5 | 32 | 0.5 | 32 | 0.5 | 32 | 0.5 | 32 |
| RMBIO (spring 2016, cold blood) | 0.5 | 32 | 0.5 | 32 | 0.5 | 32 | 0.5 | 32 | 0.5 | 32 |
| RMBIO (spring 2015, cold blood) | 0.5 | 64 | 0.5 | 32 | 0.5 | 32 | 0.5 | 32 | 0.5 | 32 |
| RMBIO (winter 2015, cold blood) | 0.5 | 32 | 0.5 | 32 | 0.5 | 32 | 0.5 | 32 | 0.5 | 32 |
| ATCC (winter 2014, mixed breed) | 0.5 | 32 | 0.5 | 32 | 0.5 | 32 | 0.5 | 32 | 0.5 | 32 |
| Central Biomedia (winter 2016, cold blood) | 0.25 | 32 | 0.25 | 32 | 0.25 | 32 | 0.25 | 32 | 0.25 | 32 |
| Central Biomedia (spring 2016, cold blood) | 0.5 | 32 | 0.5 | 32 | 0.5 | 32 | 0.5 | 32 | 0.5 | 32 |
| Central Biomedia (summer 2015, cold blood) | 0.25 | 32 | 0.25 | 32 | 0.25 | 32 | 0.25 | 32 | 0.25 | 32 |
| Central Biomedia (fall 2015, cold blood) | 0.25 | 32 | 0.25 | 32 | 0.25 | 32 | 0.25 | 32 | 0.25 | 32 |
| Lampire (spring 2016, female, thoroughbred) | 0.25 | 32 | 0.25 | 32 | 0.25 | 32 | 0.25 | 32 | 0.5 | 32 |
| Lampire (fall 2016, female, thoroughbred) | 0.25 | 32 | 0.25 | 32 | 0.25 | 32 | 0.25 | 32 | 0.5 | 64 |
| CAMHB/Vancomycin | 1 | 2 | 1 | 2 | 1 | 2 | 1 | 2 | 1 | 2 |

**Cold bloods include a mixture of Draft Horses, Belgians, Perchons and/or Clydesdales

FIGURE 6

| Time (days) | Growth Media | N | MIC$_{50}$ | MIC$_{90}$ | Range |
|---|---|---|---|---|---|
| 0 | MHB II, 25% Horse Serum, 0.5 mM DTT | 25 | 0.5 | 1 | 0.25-2 |
| 3 | | | 0.5 | 1 | 0.25-2 |
| 7 | | | 0.5 | 1 | 0.5-2 |
| 14 | | | 0.5 | 2 | 0.25-2 |
| 21 | | | 0.5 | 1 | 0.25-2 |
| 28 | | | 0.5 | 1 | 0.25-2 |

FIGURE 9

| Organism | N | MHB II, 25% Horse Serum, 0.5 mM DTT | | | Human Serum | | |
|---|---|---|---|---|---|---|---|
| | | MIC$_{50}$ | MIC$_{90}$ | Range | MIC$_{50}$ | MIC$_{90}$ | Range |
| Staphylococcus aureus | 149 | | | | | | |
| methicillin-sensitive | 74 | 0.5 | 0.5 | 0.125-1 | 0.5 | 1 | 0.25-2 |
| methicillin-resistant | 75 | 0.5 | 1 | 0.5-2 | 1 | 1 | 0.25-2 |
| Staphylococcus epidermidis (CoNS) | 54 | 0.5 | 0.5 | 0.125-2 | | | |
| Streptococcus pyogenes (Group A) | 102 | 1 | 2 | 0.5-4 | | | |
| Streptococcus agalactiae (Group B) | 101 | 1 | 2 | 0.25-4 | | | |
| Streptococcus pneumoniae | 59 | 4 | 32 | 1-64 | | | |
| Enterococcus faecalis | 23 | 16 | 256 | 0.25-256 | | | |

FIGURE 10

Range of vancomycin activity

| Organism | N | CAMHB, 25% Horse Serum, 0.5 mM DTT | | | CAMHB | | |
|---|---|---|---|---|---|---|---|
| | | MIC$_{50}$ | MIC$_{90}$ | Range | MIC$_{50}$ | MIC$_{90}$ | Range |
| Staphylococcus aureus | 149 | | | | | | |
| methicillin-sensitive | 74 | 1 | 1 | 0.5-2 | 1 | 1 | 0.5-2 |
| methicillin-resistant | 75 | 1 | 1 | 0.5-2 | 1 | 1 | 0.5-2 |
| daptomycin-resistant | 5 | 0.5 | 0.5 | 0.5-2 | | | |
| linezolid-resistant | 5 | 0.25 | 0.25 | 0.25 | | | |
| vancomycin-resistant | 13 | 0.5 | 0.5 | 0.125-1 | | | |
| vancomycin-intermediate | 13 | 2 | 16 | 0.125-32 | | | |
| Staphylococcus epidermidis (CoNS) | 54 | 0.5 | 0.5 | 0.125-2 | | | |
| Streptococcus pyogenes (Group A) | 102 | 1 | 2 | 0.5-4 | | | |
| Streptococcus agalactiae (Group B) | 101 | 1 | 2 | 0.25-4 | | | |
| Streptococcus pneumoniae | 59 | 4 | 32 | 1-64 | | | |
| Enterococcus faecalis | 23 | 16 | 256 | 0.25-256 | | | |
| Enterococcus faecium | 6 | >256 | >256 | >256 | | | |
| Acinetobacter baumannii | 13 | >512 | >512 | >512 | | | |
| Escherichia coli | 7 | >512 | >512 | >512 | | | |
| Klebsiella spp. | 5 | >512 | >512 | >512 | | | |
| Pseudomonas aeruginosa | 9 | >512 | >512 | >512 | | | |

FIGURE 11

**A. *S. aureus* ATCC 29213**
CF-301 Broth Microdilution Tier 1 MIC Quality Control
Proposed Range = 0.25-1 µg/ml (100% included)

| MIC (µg/ml) | LOT 1 | LOT 2 | LAB 1 | LAB 2 | All Labs |
|---|---|---|---|---|---|
| 0.12 | | | | | |
| 0.25 | 24 | 25 | 24 | 25 | 49 |
| 0.5 | 1 | | 1 | | 1 |
| 1 | | | | | |
| 2 | | | | | |
| 4 | | | | | |
| 8 | | | | | |
| 16 | | | | | |
| 32 | | | | | |
| 64 | | | | | |
| 128 | | | | | |
| 0 | | | | | |

| | LOT 1 | LOT 2 | LAB 1 | LAB 2 | All Labs |
|---|---|---|---|---|---|
| N | 25 | 25 | 25 | 25 | 50 |
| GEOMEAN | 0.51 | 0.50 | 0.51 | 0.50 | 0.51 |
| MODE | 0.5 | 0.5 | 0.5 | 0.5 | 0.5 |
| MIN | 0.5 | 0.5 | 0.5 | 0.5 | 0.5 |
| MAX | 1 | 0.5 | 1 | 0.5 | 1 |
| RANGE | 2 | 1 | 2 | 1 | 2 |

**B. *E. faecalis* ATCC 29212**
CF-301 Broth Microdilution Tier 1 MIC Quality Control
Proposed Range = 16-64 µg/ml (100% included)

| MIC (µg/ml) | LOT 1 | LOT 2 | LAB 1 | LAB 2 | All Labs |
|---|---|---|---|---|---|
| 0.12 | | | | | |
| 0.25 | | | | | |
| 0.5 | | | | | |
| 1 | | | | | |
| 2 | | | | | |
| 4 | | | | | |
| 8 | | | | | |
| 16 | 7 | | 7 | | 7 |
| 32 | 18 | 25 | 18 | 25 | 43 |
| 64 | | | | | |
| 128 | | | | | |
| 0 | | | | | |

| | LOT 1 | LOT 2 | LAB 1 | LAB 2 | All Labs |
|---|---|---|---|---|---|
| N | 25 | 25 | 25 | 25 | 50 |
| GEOMEAN | 26.35 | 32.00 | 26.35 | 32.00 | 29.04 |
| MODE | 32 | 32 | 32.0 | 32.0 | 32.0 |
| MIN | 16 | 32 | 16.0 | 32.0 | 16.0 |
| MAX | 32 | 32 | 32 | 32 | 32 |
| RANGE | 2 | 1 | 2 | 1 | 2 |

BROTH MICRODILUTION METHOD FOR EVALUATING AND DETERMINING MINIMAL INHIBITORY CONCENTRATION OF ANTIBACTERIAL POLYPEPTIDES

FIELD OF THE INVENTION

The present invention relates generally to components, assays and methods for evaluating antibacterial effectiveness and determining minimal inhibitory concentration (MIC) of polypeptides, including lysin polypeptides, that kill bacteria.

BACKGROUND OF THE INVENTION

The development of drug resistant bacteria is a major problem in medicine as more antibiotics are used for a wide variety of illnesses and other conditions. Novel antimicrobial therapy approaches include enzyme-based antibiotics ("enzybiotics") such as bacteriophage lysins. Phages use these lysins to digest the cell wall of their bacterial hosts, releasing viral progeny through hypotonic lysis. The high lethal activity of lysins against gram-positive pathogens makes them attractive candidates for development as therapeutics (Fischetti, V. A. (2008) Curr Opinion Microbiol 11:393-400; Nelson, D. L. et al (2001) Proc Natl Acad Sci USA 98:4107-4112). Bacteriophage lysins were initially proposed for eradicating the nasopharyngeal carriage of pathogenic streptococci (Loeffler, J. M. et al (2001) Science 294: 2170-2172; Nelson, D. et al (2001) Proc Natl Acad Sci USA 98:4107-4112).

Bacteriophage lytic enzymes have been established as useful in the assessment and specific treatment of various types of infection in subjects through various routes of administration. For example, U.S. Pat. No. 5,604,109 (Fischetti et al.) relates to the rapid detection of Group A streptococci in clinical specimens, through the enzymatic digestion by a semi-purified Group C streptococcal phage associated lysin enzyme. This enzyme work became the basis of additional research, leading to methods of treating diseases. Fischetti and Loomis patents (U.S. Pat. Nos. 5,985,271, 6,017,528 and 6,056,955) disclose the use of a lysin enzyme produced by group C streptococcal bacteria infected with a C1 bacteriophage. U.S. Pat. No. 6,248,324 (Fischetti and Loomis) discloses a composition for dermatological infections by the use of a lytic enzyme in a carrier suitable for topical application to dermal tissues. U.S. Pat. No. 6,254,866 (Fischetti and Loomis) discloses a method for treatment of bacterial infections of the digestive tract which comprises administering a lytic enzyme specific for the infecting bacteria. U.S. Pat. No. 6,264,945 (Fischetti and Loomis) discloses a method and composition for the treatment of bacterial infections by the parenteral introduction (intramuscularly, subcutaneously, or intravenously) of at least one lytic enzyme produced by a bacteria infected with a bacteriophage specific for that bacteria and an appropriate carrier for delivering the lytic enzyme into a patient.

U.S. Pat. Nos. 7,402,309, 7,638,600 and published PCT Application WO2008/018854 provides distinct phage-associated lytic enzymes useful as antibacterial agents for treatment or reduction of *Bacillus anthracis* infections. U.S. Pat. No. 7,569,223 describes lytic enzymes for *Streptococcus pneumoniae*. Lysin useful for *Enterococcus* (*E. faecalis* and *E. faecium*, including vancomycin resistant strains) are described in U.S. Pat. No. 7,582,291. US 2008/0221035 describes mutant Ply GBS lysins highly effective in killing Group B streptococci. A chimeric lysin denoted ClyS, with activity against Staphylococci bacteria, including *Staphylococcus aureus*, is detailed in WO 2010/002959. PlySs2 lysin, isolated from *Streptococcus suis* and effective in killing *Streptococcus, Staphylococcus, Enterococcus* and *Listeria* strains, is described in WO2012/145630 and U.S. Pat. No. 9,034,322.

PlySs2 lysin (CF-301) is the first lysin to enter into and complete FDA-allowed Phase I clinical trials. The lysin may be combined with standard of care antibiotics (e.g., vancomycin or daptomycin) to treat bloodstream infections, including endocarditis, caused by methicillin-sensitive and -resistant *Staphylococcus aureus*. In support of clinical trials, in vitro antibiotic susceptibility testing (AST) is utilized to evaluate and standardize the bacterial agent(s).

Broth microdilution (BMD) can be used to test lysin such as PlySs2/CF-301 activity against *S. aureus* isolates, however the standard method (CLSI methodology) is not a dependable assay and demonstrates various problems when applied to a lytic polypeptide such as PlySs2 (CF-301). The issues include a trailing effect, a disconnect or variation from susceptibility findings in human blood, serum, or plasma, and a loss of enzyme activity in frozen drug dilution panels.

In view of the deficiencies and problems associated with standard broth microdilution methods for evaluating antibacterial agents such as lysin polypeptides, there exists a need in the art for a valid, reliable and reproducible method for evaluating bacterial susceptibility in an in vitro assay that can be applied to clinical testing and evaluation and that properly mimics in vivo activity and effects.

The citation of references herein shall not be construed as an admission that such is prior art to the present invention.

SUMMARY OF THE INVENTION

The present application relates to modified methods and assays utilizing unique components for determining the minimal inhibitory concentration and assessing antibacterial killing effectiveness of peptides, particularly anti-bacterially effective peptides, particularly lytic peptides.

The invention relates to a system or assay is provided for determining MIC of an antibacterial peptide, particularly a lytic peptide, wherein the assay is conducted utilizing broth or media supplemented with mammalian serum and a reducing agent. In an aspect of the invention, an assay is provided for determining bacterial killing effectiveness of an antibacterial peptide that accurately reflects the bacterial killing effectiveness of an antibacterial peptide, such as a lytic peptide or lysin, in a mammal or patient, particularly a human.

In accordance with the invention, a method is provided for determining bacterial killing activity of an antibacterial peptide, such as a lytic polypeptide or lysin, wherein the killing activity accurately mimics the bacterial killing of said antibacterial peptide in a human, comprising evaluating an antibacterial peptide in broth supplemented with animal serum and a reducing agent. In an aspect of the invention an antibacterial peptide, such as a lytic polypeptide or lysin, is evaluated against susceptible bacteria in broth supplemented with horse serum, dog serum, rabbit serum or mouse serum and a reducing agent. In an aspect of the invention an antibacterial peptide, such as a lytic polypeptide or lysin, is evaluated against susceptible bacteria in broth supplemented with horse serum and a reducing agent.

In accordance with the invention a modified and improved broth microdilution (BMD) method and assay is provided for testing peptides, particularly anti-bacterially effective peptides, particularly lytic peptides or lysin peptides. In an aspect of the invention, a modified BMD is provided that utilizes broth or media for evaluation, wherein the broth or media is supplemented with mammalian serum and a reducing agent.

In an aspect, a modified BMD is provided that utilizes broth or media for evaluation, wherein the broth or media is supplemented with animal serum. In an aspect, a modified BMD is provided that utilizes broth or media for evaluation, wherein the broth or media is supplemented with vertebrate serum. In an aspect, a modified BMD is provided that utilizes broth or media for evaluation, wherein the broth or media is supplemented with mammalian serum. In an aspect, a modified BMD is provided that utilizes broth or media for evaluation, wherein the broth or media is supplemented with animal serum selected from horse serum, human serum, dog serum, rabbit serum, mouse serum, bovine serum. In an aspect, a broth microdilution (BMD) method is provided that utilizes broth or media for evaluation, wherein the broth or media is supplemented with animal serum selected from horse serum, dog serum, rabbit serum, mouse serum, bovine serum. In an aspect, a broth microdilution (BMD) method is provided that utilizes broth or media for evaluation, wherein the broth or media is supplemented with horse serum.

In an aspect of the BMD method of the present invention, broth or media is supplemented with mammalian serum and reducing agent. In an aspect, broth or media is supplemented with horse serum and reducing agent. In an aspect, the reducing agent is DL-Dithiothreitol (DTT). In an aspect, the reducing agent is Tris(2-carboxyethyl)phosphine hydrochloride (TCEP).

In an aspect, broth or media suitable for bacterial growth is supplemented with mammalian serum and reducing agent. In an aspect, cation-adjusted broth or media is supplemented with mammalian serum and reducing agent. In an aspect, cation-adjusted broth or media is supplemented with horse serum and reducing agent. In an aspect, the reducing agent is DL-Dithiothreitol (DTT). In an aspect, the reducing agent is Tris(2-carboxyethyl)phosphine hydrochloride (TCEP).

The amount of serum for supplementation may be determined by comparison to human serum. The amount of serum supplemented may be between 10% serum and 80% serum. In an aspect, the amount of serum supplemented may be between 10% serum and 60% serum. In an aspect, the amount of serum supplemented may be between 10% serum and 50% serum. In an aspect, the amount of serum supplemented may be between 15% serum and 40% serum. In an aspect, the amount of serum supplemented may be between 15% serum and 30% serum. In an aspect, the amount of serum supplemented may be between 20% serum and 30% serum. In an aspect, the amount of serum supplemented may be about 25% serum. In an aspect, the amount of serum supplemented is between 20% serum and 30% serum. In an aspect, the amount of serum supplemented is about 25% serum. In an aspect, the amount of serum supplemented is 25% animal serum. In an aspect, the amount of serum supplemented is about 25% horse serum.

In an aspect, broth or media is supplemented with horse serum and reducing agent. In an aspect, broth or media is supplemented with about 20% to 30% horse serum and reducing agent. In an aspect, broth or media is supplemented with about 25% horse serum and reducing agent. In an aspect, broth or media is supplemented with 25% horse serum and reducing agent. In an aspect, cation-adjusted broth is supplemented with horse serum and reducing agent. In an aspect, cation-adjusted broth is supplemented with about 20% to 30% horse serum and reducing agent. In an aspect, cation-adjusted broth is supplemented with 25% horse serum and reducing agent.

In an aspect, broth or media suitable for bacterial growth is supplemented with 25% horse serum and Dithiothreitol (DTT). In an aspect, cation-adjusted Mueller Hinton Broth (CA-MHB) is supplemented with 25% horse serum and Dithiothreitol (DTT). In an aspect, cation-adjusted Mueller Hinton Broth (CA-MHB) is supplemented with 25% horse serum and Tris(2-carboxyethyl)phosphine hydrochloride (TCEP). In an aspect, cation-adjusted Mueller Hinton Broth (CA-MHB) is supplemented with 25% horse serum and 0.5 mM DL-Dithiothreitol (DTT).

In an aspect, the amount of reducing agent is between 0.1 mM and 10 mM. In an aspect, the amount of reducing agent is between 0.1 mM and 5 mM. In an aspect, the amount of reducing agent is between 0.1 mM and 2 mM. In an aspect, the amount of reducing agent is between 0.1 mM and 1 mM. In an aspect, the amount of reducing agent is between 0.1 mM and 0.9 mM. In an aspect, the amount of reducing agent is between 0.1 mM and 0.6 mM. In an aspect, the amount of reducing agent is between 0.2 mM and 0.6 mM. In an aspect, the amount of reducing agent is between 0.3 mM and 0.6 mM. In an aspect, the amount of reducing agent is between 0.4 mM and 0.6 mM. In an aspect, the amount of reducing agent is about 0.5 mM. In an aspect, the amount of reducing agent is between 0.25 mM and 1 mM. In an aspect, the amount of reducing agent is less than 1 mM.

In an embodiment, the assay and method of the invention is used in the assessment and analysis of a lytic polypeptide. In an aspect of the invention, the BMD method with supplement(s) is utilized in determining the bacterial killing effectiveness of a lytic polypeptide active against *Streptococcus* bacteria. In an aspect of the invention, the BMD method with supplement(s) is utilized in determining the bacterial killing effectiveness of a lytic polypeptide active against *Streptococcus* and *Staphylococcus* bacteria. In an aspect of the invention, the BMD method with supplement(s) is utilized in MIC testing of a lytic polypeptide active against *Streptococcus* bacteria. In an aspect of the invention, the BMD method with supplement(s) is utilized in MIC testing of a lytic polypeptide active against *Staphylococcus* bacteria. In an aspect of the invention, the BMD method with supplement(s) is utilized in MIC testing of a lytic polypeptide active against *Streptococcus* and *Staphylococcus* bacteria. In an aspect of the invention, the BMD method with supplement(s) is utilized in MIC testing of a lytic polypeptide against gram positive bacteria. In an aspect of the invention, the BMD method with supplement(s) is utilized in MIC testing of a lytic polypeptide against more than one species of gram positive bacteria. The gram positive bacteria may be selected from *Streptococcus, Staphylococcus, Enterococcus* and *Listeria* bacteria.

In an aspect, the components, method or assay of the invention are utilized to evaluate lytic polypeptide, such as and including PlySs2 polypeptide (CF-301) or a variant or derivative thereof, against gram-positive bacteria. In an aspect, the components, method or assay of the invention are utilized to evaluate lytic polypeptide, including PlySs2 polypeptide (CF-301) or a variant or derivative thereof, against antibiotic-resistant bacteria. In an aspect, the components, method or assay of the invention are utilized to evaluate lytic polypeptide, including PlySs2 polypeptide (CF-301) or a variant or derivative thereof, against *Streptococcus* and *Staphylococcus* bacteria. In an aspect, the components, method or assay of the invention are utilized to evaluate lytic polypeptide, including PlySs2 polypeptide (CF-301) or a variant or derivative thereof, against antibiotic-resistant *Streptococcus* and/or *Staphylococcus* bacteria. In an aspect the lytic polypeptide is PlySs2 or a derivative or variant thereof. In an aspect the polypeptide comprises the sequence provided in FIG. 1 (SEQ ID NO:1).

The inclusion of mammalian serum such as horse serum is in accordance with findings as described herein that peptide, particularly lytic polypeptide, particularly an exemplary lytic polypeptide PlySs2 is more active in human sera/blood (as well as that of some other mammalian species, including horse), than in assay broth or media alone. It has been found that polypeptide, particularly an exemplary lytic polypeptide PlySs2, is significantly more active in human sera/blood (as well as that of some other species, including horse), than in cation-adjusted broth without serum added. Anti-bacterial polypeptide, particularly an exemplary lytic polypeptide PlySs2, is more active (particularly up to 32 fold to 64 fold more active) in human sera/blood (as well as that of some other species, including horse), than in broth, such as cation-adjusted broth, without serum added. When supplemented into CA-MHB at 25%, horse serum prevents the trailing effect and enables nearly identical MIC values to that obtained in 100% human serum. The supplementation with DTT serves to stabilize lysin polypeptide and enable the use of frozen micro broth dilution panels for MIC determination. DTT is a common reducing agent used to prevent the oxidation and inactivation of enzymes during storage or in the context of in vitro assays.

In an aspect of the present invention, bacteriophage lysin derived from *Streptococcus* or *Staphylococcus* bacteria are utilized in the methods and compositions of the invention. An exemplary lysin polypeptide(s) of use in the present invention, particularly PlySs2 lysin as provided herein and in FIG. 1 (SEQ ID NO: 1), are unique in demonstrating broad killing activity against multiple bacteria, particularly gram-positive bacteria, including *Staphylococcus, Streptococcus, Enterococcus* and *Listeria* bacterial strains. In one such aspect, the PlySs2 lysin is capable of killing *Staphylococcus aureus* strains and bacteria, as demonstrated herein. In an aspect, the PlySs2 lysin is capable of killing *Staphylococcus* and *Streptococcus* bacteria. PlySs2 is effective against antibiotic-resistant *Staphylococcus aureus* such as methicillin-resistant *Staphylococcus aureus* (MRSA), vancomycin resistant *Staphylococcus aureus* (VRSA), daptomycin-resistant *Staphylococcus aureus* (DRSA) and linezolid-resistant *Staphylococcus aureus* (LRSA). PlySs2 is effective against vancomycin intermediate-sensitivity *Staphylococcus aureus* (VISA).

The isolated PlySs2 lysin polypeptide may comprise the amino acid sequence provided in FIG. 1 or variants thereof having at least 80% identity, 85% identity, 90% identity, 95% identity or 99% identity to the polypeptide of FIG. 1 and effective to kill the gram-positive bacteria. The isolated PlySs2 lysin polypeptide may comprise the amino acid sequence provided in FIG. 1 or variants thereof having at least 80% identity, 85% identity, 90% identity, 95% identity or 99% identity to the polypeptide of FIG. 1 and effective to kill *Staphylococcus* and *Streptococcus* bacteria.

In any such above method or methods, the bacteria may be selected from *Staphylococcus aureus, Listeria monocytogenes, Staphylococcus simulans, Streptococcus suis, Staphylococcus epidermidis, Streptococcus equi, Streptococcus equi* zoo, *Streptococcus agalactiae* (GBS), *Streptococcus pyogenes* (GAS), *Streptococcus sanguinis, Streptococcus gordonii, Streptococcus dysgalactiae*, Group G *Streptococcus*, Group E *Streptococcus, Enterococcus faecalis* and *Streptococcus pneumonia*.

In accordance with any of the methods of the invention, bacteria may be an antibiotic resistant bacteria. The bacteria may be methicillin-resistant *Staphylococcus aureus* (MRSA), vancomycin intermediate-sensitivity *Staphylococcus aureus* (VISA), vancomycin resistant *Staphylococcus aureus* (VRSA), daptomycin-resistant *Staphylococcus aureus* (DRSA), or linezolid-resistant *Staphylococcus aureus* (LRSA). The susceptible bacteria may be a clinically relevant or pathogenic bacteria, particularly for humans. In an aspect of the method(s), the lysin polypeptide(s) is effective to kill *Staphylococcus, Streptococcus, Enterococcus* and *Listeria* bacterial strains.

In an additional aspect or embodiment of the methods and compositions provided herein, another distinct staphylococcal specific lysin is used herein alone or in combination with the PlySs2 lysin as provided and described herein. In one such aspect or embodiment of the methods and compositions provided herein, the staphylococcal specific lysin ClyS is used herein alone or in combination with the PlySs2 lysin as provided and described herein.

Other objects and advantages will become apparent to those skilled in the art from a review of the following description which proceeds with reference to the following illustrative drawings.

BRIEF DESCRIPTION OF THE DRAWINGS

FIG. 2 depicts (A) the cell wall target in *S. aureus*; (B) cleavage of the D-Ala-L-Gly bond in the staphylococcal cell wall in the peptidoglycan meshwork required for structural stability (adapted from Capot-Chartier, Front Microbiol 22:2104); and (C) cell wall hydrolysis and osmotic lysis. In (C) it is shown that peptidoglycan hydrolysis results in the osmotic lysis of the bacteria. (C) provides untreated bacteria, bacteria after 15 seconds (15 sec) with CF-301 added, and after 15 minutes with CF-301.

FIG. 4 depicts susceptibility testing results against a set of 30 *S. aureus* strains. Problems associated with certain of the assay methods are delineated.

FIG. 5 depicts tabulated results of BMD analysis of PlySs2/CF301 using the new method with 25% horse serum from 14 different sources to evaluate *S. aureus* ATCC 29213 and *E. faecalis* ATCC 29212.

FIG. 6 provides a time course of MIC determination on frozen CF-301 samples using the new BMD methodology.

FIG. 9 depicts evaluation of CF-301 MIC activity using the BMD methodology supplemented with horse serum and DTT against various susceptible gram-positive bacteria, including MRSA, MSSA, *Staphylococcus epidermidis, Streptococcus pyogenes, Streptococcus agalactiae, Streptococcus pneumoniae* and *Enterococcus faecalis.*

FIG. 10 depicts vancomycin activity assessed using the modified BMD method in comparison to method with standard CAMHB broth unsupplemented. Various *Staphylococcus aureus* strains including MSSA and MRSA strains were evaluated.

FIG. 11 provides quality control analysis of MIC determination based on BMD analysis using MHB II with 25% horse serum and 0.5 mM DTT over 5 days with (A) *S. aureus* ATCC 29213 and (B) *E. faecalis* ATCC 29212. Five replicates per strain were analyzed on consecutive days. Comparison of evaluation at two different labs Lab 1 and Lab 2 are shown. Vancomycin and oxacillin were used as control agents in CA-MHB and CA-MHB=2% saline, respectively.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

Figure 1:
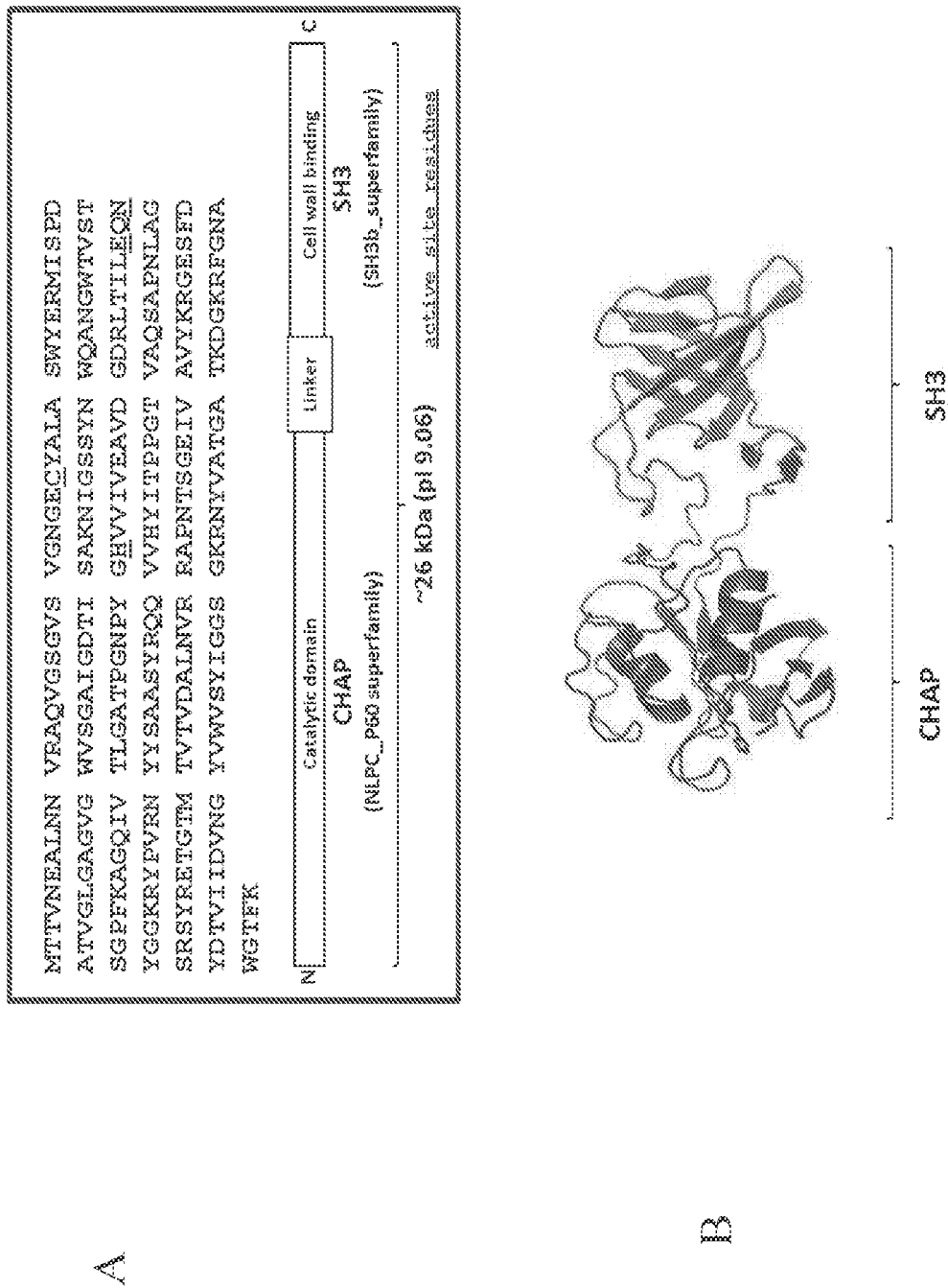
FIG. 1 depicts (A) the amino acid sequence of PlySs2 (CF-301) lysin polypeptide, with active site residues denoted, and the domain structure including the CHAP family catalytic domain and the SH3 family cell wall binding domain; and (B) a predicted 3-dimensional structure (representation by I-TASSER).

The terms "PlySs lysin(s)", "PlySs2 lysin", "PlySs2", "CF-301", "CF301" and any variants not specifically listed, may be used herein interchangeably, and as used throughout the present application and claims refer to proteinaceous material including single or multiple proteins, and extends to those proteins having the amino acid sequence data described herein and presented in FIG. 1 and SEQ ID NO: 1, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "PlySs lysin(s)", "PlySs2 lysin", "PlySs2", "CF-301", "CF301" are intended to include within their scope proteins specifically recited herein as well as all substantially homologous analogs, fragments or truncations, and allelic variations. PlySs2 lysin is described in U.S. Pat. No. 9,034,322 and PCT Application PCT/US2012/34456. Gilmer et al also describes PlySs2 lysin (Gilmer D B et al (2013) Antimicrob Agents Chemother Epub 2013 April 9 [PMID 23571534]).

The term "ClyS", "ClyS lysin" refers to a chimeric lysin ClyS, with activity against Staphylococci bacteria, including *Staphylococcus aureus*, is detailed in WO 2010/002959 and also described in Daniel et al (Daniel, A et al (2010) Antimicrobial Agents and Chemother 54(4):1603-1612). Exemplary amino acid sequence of ClyS is provided in SEQ ID NO:2.

A "lytic enzyme" or "lytic polypeptide" includes a bacterial cell wall lytic enzyme that kills one or more bacteria under suitable conditions and during a relevant time period. Examples of lytic enzymes include, without limitation, various amidase cell wall lytic enzymes. In a particular aspect, a lytic enzyme refers to a bacteriophage lytic enzyme. A "bacteriophage lytic enzyme" refers to a lytic enzyme extracted or isolated from a bacteriophage or a synthesized lytic enzyme with a similar protein structure that maintains a lytic enzyme functionality.

A lytic enzyme or lytic polypeptide is capable of specifically cleaving bonds that are present in the peptidoglycan of bacterial cells to disrupt the bacterial cell wall. It is also currently postulated that the bacterial cell wall peptidoglycan is highly conserved among most bacteria, and cleavage of only a few bonds to may disrupt the bacterial cell wall. Examples of lytic enzymes that cleave these bonds are muramidases, glucosaminidases, endopeptidases, or N-acetyl-muramoyl-L-alanine amidases. Fischetti et al (1974) reported that the C1 streptococcal phage lysin enzyme was an amidase. Garcia et al (1987, 1990) reported that the Cp1 lysin from a *S. pneumoniae* from a Cp-1 phage was a lysozyme. Caldentey and Bamford (1992) reported that a lytic enzyme from the phi 6 *Pseudomonas* phage was an endopeptidase, splitting the peptide bridge formed by *melo*-diaminopimilic acid and D-alanine. The *E. coli* T1 and T6 phage lytic enzymes are amidases as is the lytic enzyme from *Listeria* phage (ply) (Loessner et al, 1996). There are also other lytic enzymes known in the art that are capable of cleaving a bacterial cell wall.

A "lytic enzyme genetically coded for by a bacteriophage" includes a polypeptide capable of killing a host bacteria, for instance by having at least some cell wall lytic activity against the host bacteria. The polypeptide may have a sequence that encompasses native sequence lytic enzyme and variants thereof. The polypeptide may be isolated from a variety of sources, such as from a bacteriophage ("phage"), or prepared by recombinant or synthetic methods. The polypeptide may, for example, comprise a choline-binding portion at the carboxyl terminal side and may be characterized by an enzyme activity capable of cleaving cell wall peptidoglycan (such as amidase activity to act on amide bonds in the peptidoglycan) at the amino terminal side. Lytic enzymes have been described which include multiple enzyme activities, for example two enzymatic domains, such as PlyGBS lysin. Further, other lytic enzymes have been described containing only a catalytic domain and no cell wall binding domain.

"A native sequence phage associated lytic enzyme" includes a polypeptide having the same amino acid sequence as an enzyme derived from a bacterial genome (i.e., prophage). Such native sequence enzyme can be isolated or can be produced by recombinant or synthetic means.

The term "native sequence enzyme" encompasses naturally occurring forms (e.g., alternatively spliced or altered forms) and naturally-occurring variants of the enzyme. In one embodiment of the invention, the native sequence enzyme is a mature or full-length polypeptide that is genetically coded for by a gene from a bacteriophage specific for *Streptococcus suis*. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et al., J. Bacteriol. 172: 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence lytic enzyme" includes a lytic enzyme characterized by a polypeptide sequence that is different from that of a lytic enzyme, but retains functional activity. The lytic enzyme can, in some embodiments, be genetically coded for by a bacteriophage specific for a bacteria, such as *Streptococcus suis* as in the case of PlySs2, having a particular amino acid sequence identity with the lytic enzyme sequence(s), as exemplary lysin provided herein PlySs2 provided in FIG. 1. For example, in some embodiments, a functionally active lytic enzyme can kill *Streptococcus suis* bacteria, and other susceptible bacteria as provided herein, including as shown herein, by disrupting the cellular wall of the bacteria. An active lytic enzyme may have a 60, 65, 70, 75, 80, 85, 90, 95, 97, 98, 99 or 99.5% amino acid sequence identity with the lytic enzyme sequence(s) hereof, as provided in FIG. 1. Such phage associated lytic enzyme variants include, for instance, lytic enzyme polypeptides wherein one or more amino acid residues are added, or deleted at the N or C terminus of the sequence of the lytic enzyme sequence(s) hereof, as provided in FIG. 1.

In a particular aspect, a phage associated lytic enzyme will have at least about 80% or 85% amino acid sequence identity with native phage associated lytic enzyme sequences, particularly at least about 90% (e.g. 90%) amino acid sequence identity. Most particularly a phage associated lytic enzyme variant will have at least about 95% (e.g. 95%) amino acid sequence identity with the native phage associated the lytic enzyme sequence(s). An exemplary phage native sequence for the lysin PlySs2 is provided in FIG. 1.

"Percent amino acid sequence identity" with respect to the phage associated lytic enzyme sequences identified is defined herein as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity.

"Polypeptide" includes a polymer molecule comprised of multiple amino acids joined in a linear manner. A polypeptide can, in some embodiments, correspond to molecules encoded by a polynucleotide sequence which is naturally occurring. The polypeptide may include conservative substitutions where the naturally occurring amino acid is replaced by one having similar properties, where such conservative substitutions do not alter the function of the polypeptide.

The term "altered lytic enzymes" includes shuffled and/or chimeric lytic enzymes.

Phage lytic enzymes specific for bacteria infected with a specific phage have been found to effectively and efficiently break down the cell wall of the bacterium in question. The lytic enzyme is believed to lack proteolytic enzymatic activity and is therefore non-destructive to mammalian proteins and tissues when present during the digestion of the bacterial cell wall. Furthermore, because it has been found that the action of phage lytic enzymes, unlike antibiotics, was rather specific for the target pathogen(s), it is likely that the normal flora will remain essentially intact (M. J. Loessner, G. Wendlinger, S. Scherer, Mol Microbiol 16, 1231-41. (1995) incorporated herein by reference). In fact, the PlySs2 lysin, while demonstrating uniquely broad bacterial species and strain killing, is comparatively and particularly inactive against bacteria comprising the normal flora, including *E. coli*, as described herein.

A lytic enzyme or polypeptide of use in the invention may be produced by the bacterial organism after being infected with a particular bacteriophage or may be produced or prepared recombinantly or synthetically as either a prophylactic treatment for preventing those who have been exposed to others who have the symptoms of an infection from getting sick, or as a therapeutic treatment for those who have already become ill from the infection. In as much the lysin polypeptide sequences and nucleic acids encoding the lysin polypeptides are described and referenced to herein, the lytic enzyme(s)/polypeptide(s) may be preferably produced via the isolated gene for the lytic enzyme from the phage genome, putting the gene into a transfer vector, and cloning said transfer vector into an expression system, using standard methods of the art, including as exemplified herein. The lytic enzyme(s) or polypeptide(s) may be truncated, chimeric, shuffled or "natural," and may be in combination. Relevant U.S. Pat. No. 5,604,109 is incorporated herein in its entirety by reference. An "altered" lytic enzyme can be produced in a number of ways. In a preferred embodiment, a gene for the altered lytic enzyme from the phage genome is put into a transfer or movable vector, preferably a plasmid, and the plasmid is cloned into an expression vector or expression system. The expression vector for producing a lysin polypeptide or enzyme of the invention may be suitable for *E. coli, Bacillus*, or a number of other suitable bacteria. The vector system may also be a cell free expression system. All of these methods of expressing a gene or set of genes are known in the art. The lytic enzyme may also be created by infecting *Streptococcus suis* with a bacteriophage specific for *Streptococcus suis*, wherein said at least one lytic enzyme exclusively lyses the cell wall of said *Streptococcus suis* having at most minimal effects on other, for example natural or commensal, bacterial flora present.

Biologically active portions of a protein or peptide fragment of the embodiments, as described herein, include polypeptides comprising amino acid sequences sufficiently identical to or derived from the amino acid sequence of the lysin protein of the disclosure, which include fewer amino acids than the full length protein of the lysin protein and exhibit at least one activity of the corresponding full-length protein. Typically, biologically active portions comprise a domain or motif with at least one activity of the corresponding protein. For example, as depicted in FIG. 1, the PlySs2 lysin includes an N terminal CHAP domain and a C terminal SH3 domain. A biologically active portion of a protein or protein fragment can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

Mutations can be made in the amino acid sequences, or in the nucleic acid sequences encoding the polypeptides and lysins of use in the methods herein, including in the lysin sequences set out in FIG. 1, or in active fragments or truncations thereof, such that a particular codon is changed to a codon which codes for a different amino acid, an amino acid is substituted for another amino acid, or one or more amino acids are deleted. Such a mutation is generally made by making the fewest amino acid or nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

Such mutants or variants thereof may be predicted for function or tested for function or capability for killing bacteria, including Staphylococcal, Streptococcal, *Listeria*, or *Enterococcal* bacteria, and/or for having comparable activity to the lysin(s) as described and particularly provided herein. Thus, changes can be made to the sequence of lysin, and mutants or variants having a change in sequence can be tested using the assays and methods described and exemplified herein, including in the examples. One of skill in the art, on the basis of the domain structure of the lysin(s) hereof can predict one or more, one or several amino acids suitable for substitution or replacement and/or one or more amino acids which are not suitable for substitution or replacement, including reasonable conservative or non-conservative substitutions.

The PlySs2 lysin displays activity and capability to kill numerous distinct strains and species of gram positive bacteria, including Staphylococcal, Streptococcal, *Listeria*, or *Enterococcal* bacteria. In particular and with significance, PlySs2 is active in killing *Staphylococcus* strains, including *Staphylococcus aureus*, particularly both antibiotic-sensitive and distinct antibiotic-resistant strains. PlySs2 is also active in killing *Streptococcus* strains, and shows particularly effective killing against Group A and Group B *streptococcus* strains. PlySs2 lysin capability against bacteria is depicted below in TABLE 1, based on log kill assessments using isolated strains in vitro. The susceptible bacteria provided herein may be used in the modified BMD methods of the invention for determining and comparing MIC values.

TABLE 1

| PlySs2 Reduction in Growth of Different Bacteria (partial listing) | |
|---|---|
| Bacteria | Relative Kill with PlySs2 |
| *Staphylococcus aureus* (VRSA, VISA, MRSA, MSSA) | +++ |

TABLE 1-continued

| PlySs2 Reduction in Growth of Different Bacteria (partial listing) | |
|---|---|
| Bacteria | Relative Kill with PlySs2 |
| *Streptococcus suis* | +++ |
| *Staphylococcus epidermidis* | ++ |
| *Staphylococcus simulans* | +++ |
| *Lysteria monocytogenes* | ++ |
| *Enterococcus faecalis* | ++ |
| *Streptococcus dysgalactiae* - GBS | ++ |
| *Streptococcus agalactiae* - GBS | +++ |
| *Streptococcus pyogenes* - GAS | +++ |
| *Streptococcus equi* | ++ |
| *Streptococcus sanguinis* | ++ |
| *Streptococcus gordonii* | ++ |
| *Streptococcus sobrinus* | + |
| *Streptococcus rattus* | + |
| *Streptococcus oralis* | + |
| *Streptococcus pneumonine* | + |
| *Bacillus thuringiensis* | − |
| *Bacillus cereus* | − |
| *Bacillus subtilis* | − |
| *Bacillus anthracis* | − |
| *Escherichia coli* | − |
| *Enterococcus faecium* | − |
| *Pseudomanas aeruginosa* | − |

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention hereof, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which the lysin polypeptide(s) of the invention, or nucleic acid encoding such polypeptides will be, in accordance with the present invention. Polypeptides and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Polypeptides and nucleic acid may be formulated with diluents or adjuvants and still for practical purposes be isolated—for example the polypeptides will normally be mixed with polymers or mucoadhesives or other carriers, or will be mixed with pharmaceutically acceptable carriers or diluents, when used in diagnosis or therapy.

Therapeutic or pharmaceutical compositions comprising the lytic enzyme(s)/polypeptide(s) of use in the methods and applications provided in the invention may be utilized or included in the methods herein. Therapeutic or pharmaceutical compositions may comprise one or more lytic polypeptide(s), and optionally include natural, truncated, chimeric or shuffled lytic enzymes, combined with one or more antibiotics, optionally combined with suitable excipients, carriers or vehicles. The invention includes evaluation of therapeutic compositions or pharmaceutical compositions of the lysins, including PlySs2, in combination with antibiotic for use in the killing, alleviation, decolonization, prophylaxis or treatment of gram-positive bacteria, including bacterial infections or related conditions. The invention includes evaluation of therapeutic compositions or pharmaceutical compositions of the lysins, including PlySs2, in combination with vancomycin, linezolid or daptomycin.

The enzyme(s) or polypeptide(s) included in the therapeutic compositions may be one or more or any combination of unaltered phage associated lytic enzyme(s), truncated lytic polypeptides, variant lytic polypeptide(s), and chimeric and/or shuffled lytic enzymes. Additionally, different lytic polypeptide(s) genetically coded for by different phage for treatment of the same bacteria may be used. These lytic enzymes may also be any combination of "unaltered" lytic enzymes or polypeptides, truncated lytic polypeptide(s), variant lytic polypeptide(s), and chimeric and shuffled lytic enzymes. The lytic enzyme(s)/polypeptide(s) in a therapeutic or pharmaceutical composition for gram-positive bacteria, including *Streptococcus, Staphylococcus, Enterococcus* and *Listeria*, may be used alone or in combination with antibiotics or, if there are other invasive bacterial organisms to be treated, in combination with other phage associated lytic enzymes specific for other bacteria being targeted. The lytic enzyme, truncated enzyme, variant enzyme, chimeric enzyme, and/or shuffled lytic enzyme may be used in conjunction with a holin protein. The amount of the holin protein may also be varied. Various antibiotics may be optionally included in the therapeutic composition with the enzyme(s) or polypeptide(s) and with or without the presence of lysostaphin. More than one lytic enzyme or polypeptide may be included in the therapeutic composition.

The pharmaceutical composition can also include one or more altered lytic enzymes, including isozymes, analogs, or variants thereof, produced by chemical synthesis or DNA recombinant techniques. In particular, altered lytic protein can be produced by amino acid substitution, deletion, truncation, chimerization, shuffling, or combinations thereof. The pharmaceutical composition may contain a combination of one or more natural lytic protein and one or more truncated, variant, chimeric or shuffled lytic protein. The pharmaceutical composition may also contain a peptide or a peptide fragment of at least one lytic protein derived from the same or different bacteria species, with an optional addition of one or more complementary agent, and a pharmaceutically acceptable carrier or diluent.

Therapeutic or pharmaceutical compositions may comprise lytic polypeptide(s) combined with a variety of carriers to treat the illnesses caused by the susceptible gram-positive bacteria. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts. Glycerin or glycerol (1,2,3-propanetriol) is commercially available for pharmaceutical use. DMSO is an aprotic solvent with a remarkable ability to enhance penetration of many locally applied drugs. The carrier vehicle may also include Ringer's solution, a buffered solution, and dextrose solution, particularly when an intravenous solution is prepared.

The lytic enzyme/polypeptide(s) should be in an environment having a pH which allows for activity of the lytic enzyme/polypeptide(s). A stabilizing buffer may allow for the optimum activity of the lysin enzyme/polypeptide(s). The stabilizing buffer may also be or include a metal chelating reagent, such as ethylenediaminetetracetic acid disodium salt, or it may also contain a phosphate or citrate-phosphate buffer, or another suitable buffer.

The term 'agent' means any molecule, including polypeptides, antibodies, polynucleotides, chemical compounds and small molecules. In particular the term agent includes compounds such as test compounds, added additional compound(s), or lysin enzyme compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, polypeptide, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The terms "gram-positive bacteria", "Gram-positive bacteria", "gram-positive" and any variants not specifically listed, may be used herein interchangeably, and as used throughout the present application and claims refer to Gram-positive bacteria which are known and/or can be identified by the presence of certain cell wall and/or cell membrane characteristics and/or by staining with Gram stain. Gram positive bacteria are known and can readily be identified and may be selected from but are not limited to the genera *Listeria, Staphylococcus, Streptococcus, Enterococcus, Mycobacterium, Corynebacterium*, and *Clostridium*, and include any and all recognized or unrecognized species or strains thereof. In an aspect of the invention, the PlyS lysin sensitive gram-positive bacteria include bacteria selected from one or more of *Listeria, Staphylococcus, Streptococcus*, and *Enterococcus*.

Gram-positive bacteria are surrounded by a cell wall containing polypeptides and polysaccharide. Gram-positive bacteria include but are not limited to the genera *Actinomyces, Bacillus, Listeria, Lactococcus, Staphylococcus, Streptococcus, Enterococcus, Mycobacterium, Corynebacterium*, and *Clostridium*. Medically relevant species include *Streptococcus pyogenes, Streptococcus pneumoniae, Staphylococcus aureus*, and *Enterococcus faecalis*. *Bacillus* species, which are spore-forming, cause anthrax and gastroenteritis. Spore-forming *Clostridium* species are responsible for botulism, tetanus, gas gangrene and pseudomembranous colitis. *Corynebacterium* species cause diphtheria, and *Listeria* species cause meningitis.

The term "bacteriocidal" refers to capable of killing bacterial cells.

The term "bacteriostatic" refers to capable of inhibiting bacterial growth, including inhibiting growing bacterial cells.

The phrase "pharmaceutically acceptable" refers to molecular entities and compositions that are physiologically tolerable and do not typically produce an allergic or similar untoward reaction, such as gastric upset, dizziness and the like, when administered to a human.

The term "reducing agent" refers to and includes a substance that causes another substance to undergo reduction and that is oxidized in the process. A reducing agent may serve to keep enzymes or proteins in a reduced state and to prevent oxidation thereof. In an aspect a reducing agent maintains stability of a polypeptide or enzyme, including with storage over a period of time or under different conditions.

One skilled in the art will be aware of established or recognized reducing agent, particularly those of use and accepted for use in assays, including clinical assays. Examples of reducing agents include Dithiothreitol (DTT), Tris(2-carboxyethyl)phosphine hydrochloride (TCEP), Lithium aluminum hydride (LiAlH$_4$), Sodium borohydride (NaBH$_4$), diborane, beta mercaptoethanol (BME), and Diisobutylaluminum hydride (DIBAL-H).

Broth or media suitable for use and application in the methods and assays of the invention includes broth or media for growth and maintenance of bacteria as accepted and known to one skilled in the art or any such general-purpose medium that may be used in the cultivation of a wide variety of microorganisms and includes, but is not limited to, the broth or media utilized and/or described herein. Exemplary broth or media include cation-adjusted broth suitable for quantitative procedures for antimicrobial susceptibility testing.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Lysins are antimicrobial enzymes that provide a novel alternative to conventional antibiotics. Lysins are proteins encoded by bacteriophages and used to kill bacteria in a natural setting. There are about $10^{31}$ phage in the biosphere and phage kill approximately one-third of all bacteria daily with the lysin protein family the primary means to kill host bacteria (Hatful G F (2015) J Virol 89(16):8107-8110). Purified lysins exhibit the phenomenon called "lysis from without" (Fischetti V A et al (20016) Nature Biotechnology 24:1508-1511) and are amendable to synthetic recombinant manufacture. Purified lysins exhibit potent bacteriolytic effect on contact via cell wall hydrolysis. Lysin polypeptides are typically a 20-30 kDa protein.

PlySs2 lysin (also denoted as CF-301) represents the first and only lysin to enter human clinical trials in the U.S. CF-301 was granted fast track status by the FDA for *Staphylococcus aureus* bacteremia and a Phase I trial was completed in 2015. PlySs2 was originally derived from a prophage carried by *Streptococcus suis* in pigs. PlySs2 lysin has been demonstrated to kill various strains of clinically significant gram-positive bacteria, including antibiotic resistant strains such as methicillin and vancomycin resistant and sensitive strains of *Staphylococcus aureus* (MRSA, MSSA, VRSA, VISA), daptomycin-resistant *Staphylococcus aureus* (DRSA), and linezolid-resistant *Staphylococcus aureus* (LRSA). PlySs2 is a unique lysin in having comparatively broad but defined species killing activity and can kill multiple species of bacteria, particularly gram-positive bacteria, including *Staphylococcus, Streptococcus, Enterococcus* and *Listeria* bacterial strains, while being inactive against bacteria in the natural intestinal flora.

Clinical grade PlySs2/CF-301 has been produced recombinantly in *E. coli* and is active over broad pH (pH 6-9.7) and temperature (16-55° C.) ranges (Gilmer et al (2013) Antimicrob Agents Chemother 57:2743-2750; Scuch et al (2014) J Infect Dis 209:1469-78). It is active in various human matrices including blood, serum, plasma, saliva, synovial fluid, pulmonary surfactant and bronchial lavage fluid. The amino acid sequence and structure of PlySs2 (CF-301) is provided in FIG. 1.

PlySs2 (CF-301) targets the cell wall of sensitive bacteria, including *Staphylococcus aureus*. It is a cysteine-histidine aminopeptidase that targets the D-Ala-L-Gly bond in the cell wall peptidoglycan and cleaves between D-alanine (stem peptide) and L-glycine (cross-bridge) of the cell wall (FIG. 2). Bacterial lysis is rapid (FIG. 2C). CF-301 has defined species specificity and kills antibiotic resistant bacteria including MSSA, MRSA, VRSA, DRSA and LRSA, bacteria resistant to methicillin, vancomycin, daptomycin, linezolid antibiotics (Schich R et al (2014) J Infect Dis 209: 1469-1478). Killing is rapid and potent and a low resistance profile to the lytic peptide is seen. CF-301 eradicates biofilms and kills persistant pacteria. Synergy with antibiotics has been observed.

In order to provide a reproducible and consistent evaluation of lytic polypeptide effects on bacteria including in a clinical trial setting, we have evaluated various methods and developed a broth microdilution (BMD) method which is an alteration of the BMD method in accordance with standards as described in the Clinical and Laboratory Standards Institute (CLSI) document M07-A9 (Methods for dilutional antimicrobial sensitivity tests for bacteria that grow aerobically. Volume 32 (Wayne [PA]: Clinical and Laboratory Standards Institute [US], 2012).

We have found that the standard CLSI methodology must be modified in order to abrogate issues in MIC determination of lytic polypeptides, particularly including PlySs2 (CF-301) including the following three major issues: 1) a trailing effect; 2) a distinct disconnect from susceptibility findings in human blood, serum, or plasma; and 3) a loss of enzyme activity in the frozen drug dilution panels. Following extensive assay development, a modified BMD method has been developed to provide accurate, reproducible and robust susceptibility testing. The new method adheres as closely to CLSI standards as possible and is optimized for use in the routine clinical laboratory.

Lytic polypeptide, such as and including PlySs2 (CF-301), has presented challenges with susceptibility testing. PlySs2/CF-301 is a large bacteriolytic enzyme, distinct from antibiotics with respect to physical characteristics, mode of action, and metabolism. Several factors may impede accurate susceptibility testing: Compound size (26 kDa) and charge (pI of 9.2) limits diffusion on solid surfaces; Thiol group (active-site cysteine) can be oxidized and inactivated (half-life in MHB is ~5 h); Net positive charge mediates "sticking" to polystyrene surfaces (less so to polypropylene); Trailing (or Eagle) effect for ~70% of S. aureus strains using broth microdilution (BMD); MIC disconnects between CA-MHB ($MIC_{90}$ of 64 µg/ml) and human blood/serum/plasma ($MIC_{90}$=1 µg/ml). Therefore an alternative BMD method was sought to enable accurate susceptibility testing for lytic polypeptides, such as and including PlySs2/CF-301.

Figure 3:
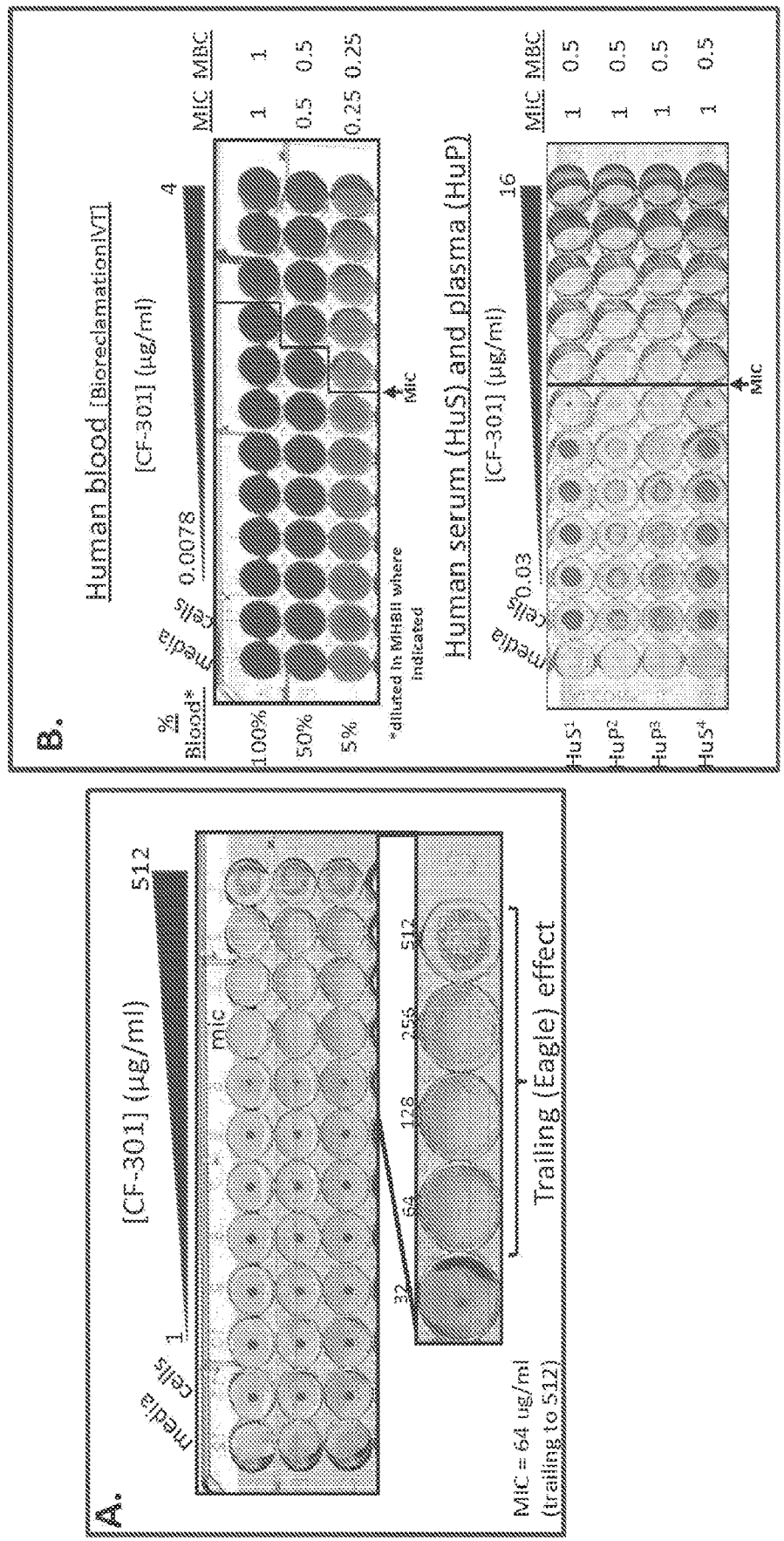
FIG. 3 provides examples of trailing and blood effects in BMD assays. (A) trailing or Eagle effect obscures accurate MIC determinations in MHBII. (B) Blood effect with *S. aureus* strain is depicted. Human serum (HuS) and plasma (HuP) utilized are as follows: HuS[1]=pooled male AB, Innovative Research, Inc; HuS[2]=pooled normal, Innovative Research, Inc; HuS[3]=individual normal, Bioreclamation-IVT; HuS[4]=pooled male AB, Sigma-Aldrich.

Examples of the problems of trailing and blood effects in standard CLSI BMD assays are shown in FIG. 3. Standard BMD analysis of S. aureus ATCC 700699 was conducted in CA-MHB (FIG. 3A) and in human blood matrices (FIG. 3B). A trailing or Eagle effect was found that obscures accurate MIC determinations in standard broth Mueller Hinton Broth II (MHBII) (FIG. 3A). Although the MIC value under these standard conditions is 64 µg/ml, trailing and Eagle effects were observed up to 512 µg/ml. It was found that CF-301 is far more potent in human blood, plasma and serum than in MHBII (FIG. 3B). The MIC value in human blood is 1 µg/ml. Thus, it was demonstrated that MHBII is not sufficient for susceptibility testing and that supplements or modifications to standard broth microdilution testing may help achieve MIC values similar to that in human matrices.

Two modified BMD methods were initially developed to test PlySs2/CF-301. In the first method, the major modifications were that polypropylene plates were used and MHBII was supplemented with 1 mM DTT. DTT (DL-Dithiothreitol) is a common molecular biology reagent used to keep enzymes in a reduced state. Using this stopgap method, 223 contemporary clinical MSSA and MRSA strains were examined with $MIC_{90}$=8 µg/ml determined (range=1-16 µg/ml). This procedure was a stop gap because of the use of polypropylene, a remaining disconnect from human blood MIC values, and problems with frozen panels.

To determine the next method, a superior method, polystyrene plates and CA-MHB were utilized. A panel of 30 S. aureus strains were screened using numerous procedural variations and supplements (known to influence AST performance) for the ability to support human blood-like activity and enable use of frozen panels. The following were evaluated:

Different animal sera (5-50%)—dog, rabbit, horse, mouse serum
Laked horse blood (1-5%)
DTT (0.05-5 mM)
Animal sera (5-50%)+DTT (0.5 mM)
Tween 80 (0.002%)
BSA (0.05-0.5%)
NaCl (1-5%)
BSA 0.1%, NaCl 2%, agitation at 200 $rpm^2$
BSA 0.1%, NaCl 2%
$CaCl_2$ (to 50 µg/ml)
$MgCl_2$ (to 50 µg/ml)
$CaCl_2$ (to 50 µg/ml)+$MgCl_2$ (to 50 µg/ml)
TCEP (0.01-5 mM)
various broth and media—LB, TSB, BHI, ¼ MHB, ½ MHB
pH, inoculum, and atmospheric variations Results from the procedural variations are provided below in TABLE 2.

TABLE 2

Identification of new BMD testing conditions

| Growth Medium | Dilutions* | $MIC_{50}$ | $MIC_{90}$ | Range | Trailing | Problems |
|---|---|---|---|---|---|---|
| 100% Human Serum | Fresh | 0.5 | 1 | 0.125-2 | none | Human blood product |
| CAMHB | Fresh | 32 | 64 | 2-128 | strong | Trailing and freezing |
|  | Thawed | 128 | 256 | 32-->256 | strong |  |
| CAMHB, 25% horse serum | Fresh | 1 | 2 | 0.5-4 | none | Freezing |
|  | Thawed | 2 | 2 | 0.5-8 | none |  |
| CAMHB, 0.5 mM DTT | Fresh | 128 | 128 | 8-256 | strong | Trailing and freezing |
|  | Thawed | 128 | 256 | 64-->356 | strong |  |
| CAMHB, 25% horse serum, 0.5 mM DTT | Fresh | 0.5 | 1 | 0.25-2 | none | NONE |
|  | Thawed | 0.5 | 1 | 0.25-2 | none |  |

*Distinguishes between the use of freshly diluted CF-301 panels and frozen-thawed CF-301 dilutions panels On the basis of the above evaluations, supplements for a new BMD method were determined. Horse serum and reducing agent (DTT) were utilized that enable human serum-like levels of activity and allow the use of frozen lysin polypeptide (CF-301) dilution panels. In particular 25% horse serum and 0.5 mM DTT was supplemented for satisfactory MIC results. Relevant susceptibility testing results against a set of 30 S. aureus strains are tabulated in FIG. 4. For freeze-thaw a standard 2-fold dilution scheme for CF-301 was utilized in the indicated medium with freezing at −70° C. for 24 hr before thawing, adding bacteria, and determining MICS. The BMD methodology utilized is further detailed in the procedure provided below.

To validate the horse serum/DTT method, fresh and thawed CF-301 dilution panels, using various BMD conditions and supply sources, were assessed against 25 *S. aureus* strains. Modifications of conditions and sources were as follows:

- Analysis on 5 consecutive days, performed by 2 different individuals
- Various sources of horse serum (Sigma, Corning, Gibco, BioreclamationlVT, Mediatech, RAMBIO, ATCC, Central Biomedia, Lampire)
- Various sources each of powder CA-MHB/MHB II (BD and Sigma) and pre-made liquid MHB II (BD and Teknova)
- Multiple sources of DTT (Sigma (liquid,powder), G-Biosciences)
- Growth temperatures of 30-37° C. in ambient air, 37° C. in 5% CO2, plate agitation up to 200 rpm
- A final/optimum media pH range of 7.4±0.6 was determined
- A final/optimum inoculum (CFU/ml) range of $5 \times 10^5 \pm 1$-log 10

Some exemplary results of the source and conditions evaluations are provided below in TABLES 3, 4 and 5. A study comparing BMD analysis of *S. aureus* ATCC 29213 and *E. faecalis* ATCC 29212 on five consecutive days using 14 difference sources of horse serum is provided in FIG. 5.

TABLE 3

Effect of varying DTT sources on MIC(ug/mL)

| Source | N | Freeze/Thaw | $MIC_{50}$ | MIC | Range |
|---|---|---|---|---|---|
| Sigma (liquid) | 25 | no | 0.5 | 1 | 0.25-2 |
|  | 25 | yes | 0.5 | 1 | 0.25-2 |
| Sigma (powder) | 25 | no | 0.5 | 1 | 0.25-2 |
|  | 25 | yes | 0.5 | 1 | 0.25-2 |
| G-Biosciences (powder) | 25 | no | 0.5 | 1 | 0.25-2 |
|  | 25 | yes | 0.5 | 1 | 0.25-2 |

TABLE 4

Effect of varying CAMHB sources on MIC (ug/mL)

| Source | N | Freeze/Thaw | $MIC_{50}$ | $MIC_{90}$ | Range |
|---|---|---|---|---|---|
| BBL ™ BD (Powder) | 25 | no | 0.5 | 1 | 0.25-2 |
|  | 25 | yes | 0.5 | 1 | 0.25-2 |
| Teknova (Liquid) | 25 | no | 0.5 | 1 | 0.25-1 |
|  | 25 | yes | 0.5 | 1 | 0.25-1 |
| BD (Liquid) | 25 | no | 0.5 | 1 | 0.25-1 |
|  | 25 | yes | 0.5 | 1 | 0.25-1 |
| Sigma-Aldrich (Powder) | 25 | no | 1 | 2 | 0.5-2 |
|  | 25 | yes | 1 | 2 | 0.5-2 |

TABLE 5

Effect of varying incubation conditions on MIC (ug/mL)

| Condition | Modification | N | $MIC_{50}$ | $MIC_{90}$ | Range |
|---|---|---|---|---|---|
| Final pH | Unadjusted (pH 7.4) | 25 | 0.5 | 1 | 0.25-2 |
|  | Adjusted to pH 7.0 |  | 0.5 | 1 | 0.25-2 |
|  | Adjusted to pH 8.0 |  | 1 | 1 | 0.25-2 |
| Bacterial inoculum | $5 \times 10^6$ CFU/ml | 25 | 0.5 | 1 | 0.25-1 |
|  | $5 \times 10^5$ CFU/ml |  | 0.5 | 1 | 0.25-2 |
|  | $5 \times 10^5$ CFU/ml |  | 0.5 | 1 | 0.25-2 |
|  | $5 \times 10^4$ CFU/ml |  | 0.5 | 1 | 0.25-1 |
| Incubation condition | Ambient air (37° C.) | 25 | 0.5 | 1 | 0.25-2 |
|  | Ambient air (30° C.) |  | 0.5 | 1 | 0.25-1 |
|  | 5% $CO^2$ (37° C.) |  | 0.5 | 1 | 0.25-2 |

All modifications tested yielded a ≤2-fold variance from $MIC_{5w90}$ of 0.5/1 µg/ml (range=0.25-2). Also, prolonged incubation of CF-301 panels at −80° C. had no significant effect (assayed up to 365 days at present) (TABLE 6). A time course of activity of frozen samples is provided in FIG. 6.

TABLE 6

Impact of long-term storage at −80° C.

| Time (days) | N | $MIC^{50}$ | $MIC^{90}$ | Range |
|---|---|---|---|---|
| 1 | 25 | 0.5 | 0.5 | 0.25-1 |
| 3 | 25 | 0.5 | 1 | 0.25-2 |
| 7 | 25 | 0.5 | 0.5 | 0.25-1 |
| 14 | 25 | 0.5 | 1 | 0.25-2 |
| 60 | 25 | 0.5 | 0.5 | 0.25-2 |
| 90 | 25 | 0.5 | 1 | 0.25-2 |
| 120 | 25 | 0.5 | 1 | 0.25-2 |
| 180 | 25 | 0.5 | 0.5 | 0.25-1 |
| 365 | 25 | 0.5 | 0.5 | 0.25-2 |

Figure 7:
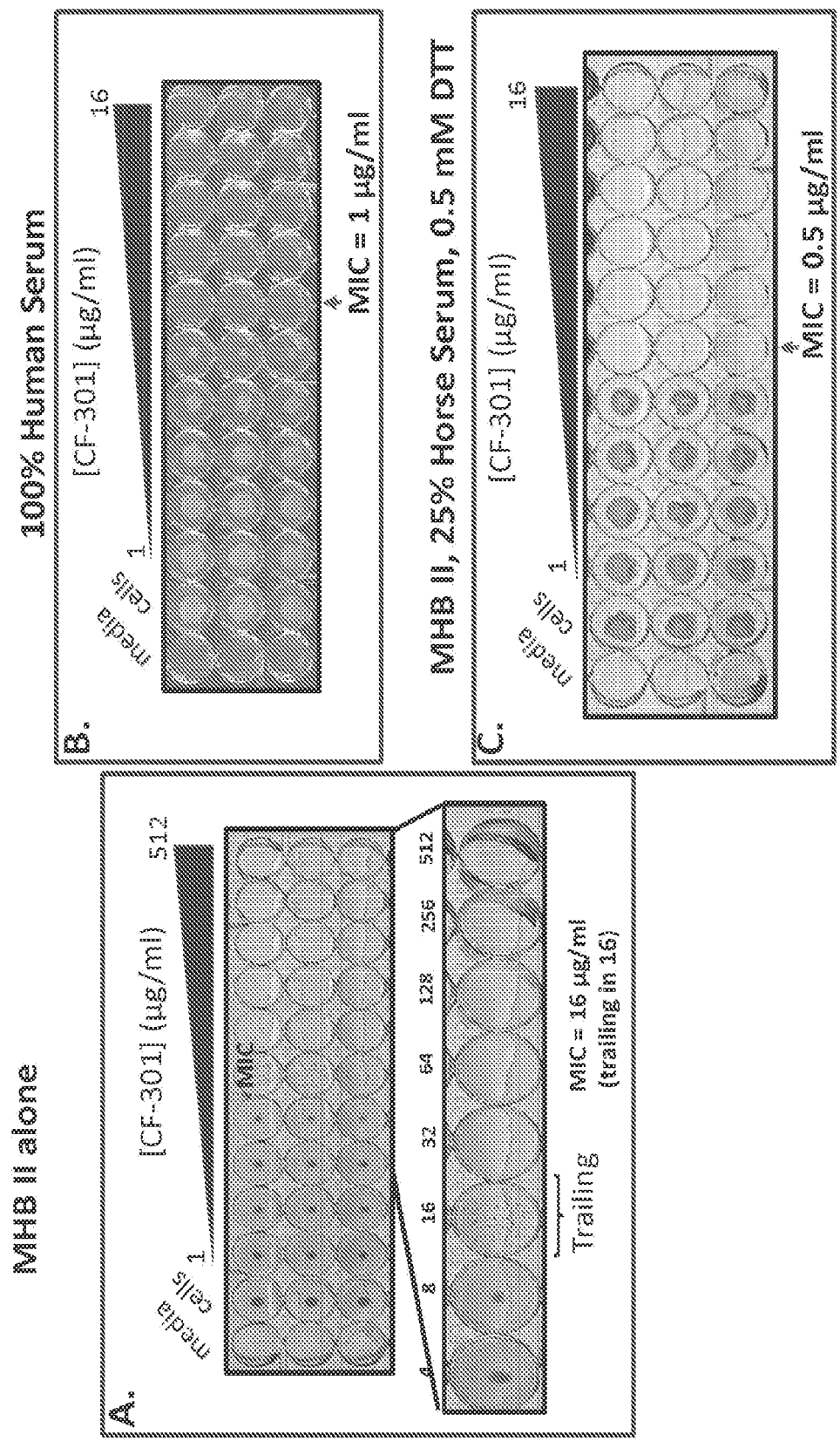
FIG. 7 depicts MIC assays of MRSA strain ATCC 29213 under different conditions. (A) MHBII alone (MIC=16 µg/ml, with slight trailing effect); (B) 100% human serum (MIC=1 µg/ml); and (C) MHBII, 25% horse serum, 0.5 mM DTT (MIC=0.5 µg/ml).

MIC assays using MHBII alone, 100% horse serum alone and in BHBII supplemented with horse serum and DTT were conducted using MRSA strain ATCC 29213 under different conditions (FIG. 7). MHBII alone gave a MIC of 16 µg/ml, with slight trailing effect. BMD assay in 100% human serum gave MIC=1 µg/ml, and in MHBII supplemented with 25% horse serum, 0.5 mM DTT the MIC was close to that of human serum with a MIC of 0.5 µg/ml.

Figure 8:
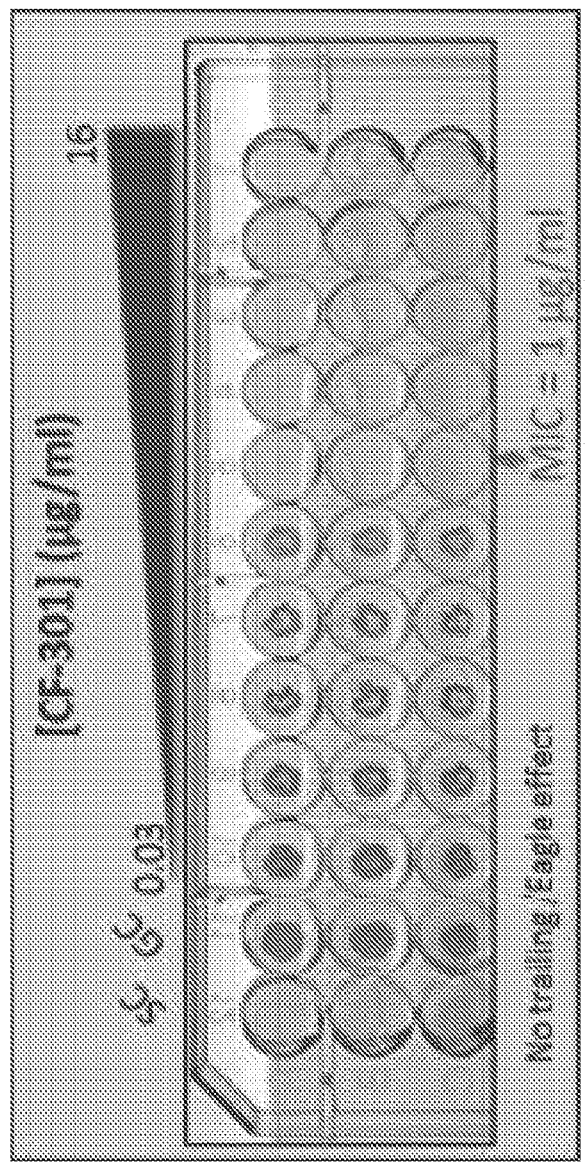
FIG. 8 depicts MIC assay of *S. aureus* strain ATCC 700699 in CA-MHB with 25% horse serum and 0.5 mM DTT (MIC=1 µg/ml).

A similar MIC assay analyzing *S. aureus* ATCC 70069 using the new method in CA-MHB supplemented with 0.25% horse serum and 0.5 mM DTT showed no trailing or Eagle effect and a MIC of 1 µg/ml, mimicking that of human serum (FIG. 8).

To further evaluate the BMD method using MHBII supplemented with 25% horse serum, 0.5 mM DTT a large set of clinical MSSA and MRSA isolates were evaluated and compared to 100% human serum for MIC determination. The analysis was also extended to various gram-positive pathogens previously demonstrated to be susceptible to PlySs2 lysin (CF-301) (Schich et al (2014) J Infect Dis 209:1469-1478), including *Staphylococcus epidermidis, Streptococcus pyogenes, Streptococcus agalactiae, Streptococcus pneumoniae* and *Enterococcus faecalis*. The results are shown in FIG. 9. CF-301 maintains its spectrum of activity using the new methodology.

Standard antibiotic vancomycin was evaluated in the modified BMD method. The $MIC_{50}$, $MIC_{90}$ and range were equivalent using standard CA-MHB versus CA-MHB supplemented with horse serum and DTT (FIG. 10).

In an effort to further evaluate the new BMD method, analysis was performed at a distinct testing locations, including the inventor laboratory and a secondary location the Clinical Microbiology Institute (CMI; Wilsonville, Oreg.) to confirm repeatability of the results by others. QC strains used for assessment included *S. aureus* ATCC 29213 and *E. faecalis* ATCC 29212. BMD analysis using MHB II with 25% horse serum and 0.5 mM DTT was conducted over 5 days with *S. aureus* ATCC 29213 and *E. faecalis* ATCC 29212 (FIG. 11). Five replicates per strain were analyzed on five consecutive days. The assay was repeatable over 5 consecutive days and between laboratories.

Figure 12:
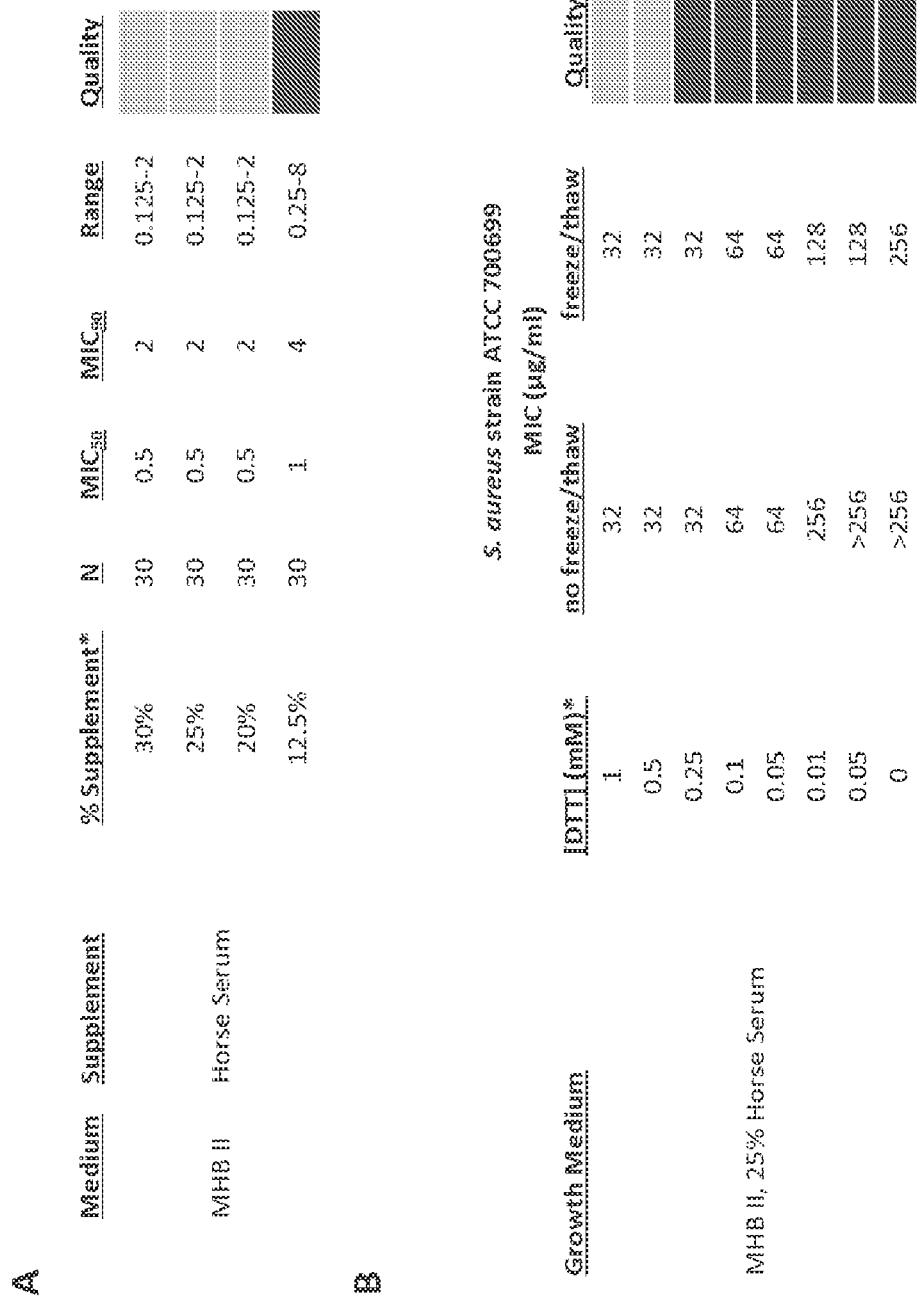
FIG. 12 depicts range finding studies evaluating (A) various amounts of horse serum supplement (12.5% to 30%) and (B) varying amounts of reducing agent DTT supplement (0-1 mM). Quality is designated as either dark tone or lighter tone. If dark, the method was disqualified based on trailing effect, high MIC values (compared to human serum (HuS), or inability to be frozen. Lighter tone indicates that the method provides an HuS-like level of activity.

Range finding experiments were conducted evaluating varying amounts of serum and reducing agent supplement. Results evaluating horse serum between 12.5% and 30% and evaluating DTT between 0 and 1 mM supplement are depicted in FIG. 12. Conditions were based on the ability to mimic human serum-like activity. In serum assays, each condition used the same set of 30 *S. aureus* strains. In DTT assays, a single *S. aureus* strain was used for a range of conditions. Quality was assessed and is indicated. Horse serum supplement levels at 20% through 30% were suitable. Horse serum at 12.5% gave unsatisfactory results. DTT is suitable between 0.25 and 1 mM, with 0.5 mM and 1 mM most ideal because of trailing effect or high MIC or inability to be frozen with 0.25 mM DTT or less. The studies were also conducted with an alternative reducing agent TCEP and gave similar results to DTT.

In summary, accurate in vitro BMD testing of lytic polypeptides, such as and particularly PlySs2(CF-301), requires two supplements: serum and a reducing agent. In the present instance, BMD evaluation with horse serum and DTT from various sources as supplements provides accurate results across numerous strains of bacteria, including various *S. aureus* strains and *E. faecalis*. The added mammalian serum, particularly horse serum, removes the trailing effect and enables quantification of activity comparable to that observed in human blood, serum, or plasma. The addition of a reducing agent, such as particularly DTT, stabilizes the lysin and serves to prevent oxidation and enable use of frozen lytic polypeptide dilution panels. The present modified BMD method is accurate, repeatable and robust.

A detailed exemplary method and procedure for the modified BMD assay is described in more detail below.

Broth Microdilution Procedure:

The general procedure for performing broth-microdilution susceptibility testing is provided in this section. The procedure is a variation of CLSI methodology (document M07-A9, 2015) and is based on the method described by Wiegand et al., 2008 (see Appendix D, Section D1) to examine the MIC of highly charged antimicrobial peptides.

Preparing Diluted Lytic Polypeptide for Analysis:

Lytic polypeptide (PlySs2) is provided as a frozen stock solution suspended at concentration of 10.74 mg/ml in Demo buffer. Demo buffer is sodium phosphate monobasic dihydrate (7.67 mM), sodium phosphate dibasic dihydrate (7.33 mM), and sodium chloride (150 mM) at a pH of 7.22. For establishing PlySS2 dilutions, the diluent utilized was MHB II supplemented with 25% horse serum and 0.5 mM DTT. Each strain or isolate is examined in triplicate, with two strains or isolates per plate.

1. Thaw frozen lysin polypeptide (e.g. CF-301) stock solution by suspension for 5 minutes in a 24° C. waterbath. Store thawed sample on ice until use within no more than 30 minutes. Discard unused polypeptide (CF-301).
2. Decide on the desired two-fold lysin polypeptide (e.g. CF-301) dilution range needed for assay. For most *Staphylococcus aureus* strains, the range will begin with a final desired concentration of 8 or 16 µg/ml. For some vancomycin-intermediate *S. aureus* strains, the range will begin with 512 µm/ml.
3. Prepare lysin polypeptide (e.g. CF-301) master dilution stocks at twice the desired final concentration for each dilution and fill the appropriate wells of columns 1-10 with 0.05 ml. Pipette 0.1 ml of broth into the wells of column 12 to serve as a sterility control and pipette 0.05 ml into the wells of column 11 to serve as the growth control.

Inoculum Preparation and Inoculation:

To standardize the inoculum density for a susceptibility test, a McFarland Equivalence Turbidity Standard (Remel, Catalog Number R20421) was utilized. On each day of testing, quality control strains are utilized, as an example the following quality control strains: *S. aureus* ATCC 29213 (CFS-581), *S. aureus* ATCC 43300 (CFS-553), and *E. faecalis* ATCC 29212 (CFS-806).

1. Prepare the inoculum by making a direct broth suspension of isolated colonies selected from an 18-24 hour blood agar plate. Broth suspension can be performed in BBL™ Mueller Hinton Broth, 2 ml Tubes (BD Diagnostic Systems, Catalog Number 296164).
2. Adjust the suspension to achieve a turbidity equivalent to a 0.5 McFarland standard using the DEN-1 Densitometer from Grant Instruments.
3. Within 15 minutes of preparation, dilute the adjusted inoculum into broth so, after inoculation, each well will contain a final concentration of approximately $5\times10^5$ CFU/ml. Since the inoculum volume for each well of columns 1-11 will be 0.05 ml, the 0.5 McFarland suspension should be diluted 1:100 to yield $1\times10^6$ CFU/ml. When 0.05 ml of this suspension is inoculated into the microtiter plate wells (already containing 0.05 ml), the final test concentration of bacteria is approximately $5\times10^5$ CFU/ml.
4. Within 15 minutes after the inoculum has been standardized as described above, inoculate each well of columns 1-11 with 0.05 ml. The final volume of each well is now 0.1 ml.
5. Perform a purity check of the inoculum suspension by subculturing an aliquot onto a blood agar plate for simultaneous incubation.

Incubation:

The inoculated trays are incubated at 37° C. for 16 to 18 hours in an ambient air incubator within 15 minutes of adding the inoculum. It is recommended to not stack plates more than four high.

Determine MIC End Points:

1. Compare the amount of growth in the wells containing CF-301 with the amount of growth in the growth control well. For the test to be considered valid, acceptable growth must occur in the growth control well. Determine MIC values by eye.
2. As an independent record, read and save the $OD_{600}$ values for the wells of each tray determined in a Molecular Devices SpectraMax M3 platereader.

Media and Supplements

Supplements

DL-Dithiothreitol (DTT) Stock Solution (1M) from Powder
1. Dissolve 1.5 g of DTT into 1 ml $H_2O$ (UltraPure DNase/RNase-Free Distilled Water)
2. Bring the volume to 10 ml with distilled water and sterilize by passage through a 0.22 µm filter
3. Prepare on the day of use (do not store and reuse)

DL-Dithiothreitol (DTT) Solution (1 M in $H_2O$)
1. Aseptically open the glass vial and dispense appropriate amount
2. Prepare on the day of use (do not store and reuse)

Horse Serum (100%)
1. Thaw frozen horse serum either overnight at 4° C. or over a 1 hour incubation at 24° C.

2. Aseptically add appropriate amount of serum to autoclaved and cooled MHB II broth
3. Store frozen at −20° C. in 50 ml aliquots Agar Media Tryptic Soy Agar with 5% Sheep Blood
Obtain premade Tryptic Soy Agar plates (supplemented with 5% Sheep Blood) from a commercially available source Broth Media Cation-Adjusted Mueller Hinton Broth
Obtain dehydrated Mueller Hinton II Broth (Cation Adjusted) from a commercially available source.
This form should contain 20-25 mg of $Ca^{2+}$/L and 10-12.5 mg of $Mg^{2+}$/L.
1. Prepare MHB II exactly according to manufacturer's recommendations, autoclave, cool to 55° C. for 1 hour, sterile-filter by passage through a 0.22 μm membrane, and chill overnight at 2 to 8° C.
2. Check pH. The final pH should be 7.2-7.4.
3. Store at 2 to 8° C. protected from the light for no longer than 1 week.

Cation-Adjusted Mueller Hinton Broth with 25% Horse Serum and 0.5 mM DTT
1. Prepare cation-adjusted Mueller Hinton Broth as described in Section B3.1.
2. After chilling broth overnight at 2 to 8° C., add 25 ml of horse blood to 75 ml of broth for each 100 ml needed. See Section B1.2 for preparation of horse blood.
3. Gently swirl to mix.
4. After mixing, add 0.05 ml of 1M DTT stock solution for each 100 ml of Broth+25% horse serum needed. Depending on the source of DTT, see Sections B1.1 or B1.2 for preparation.
5. The final pH should be 7.4
6. Prepare fresh media only on the day of use. Do not store media and reuse.

Reagents and Equipment
Bacterial Growth Media
BBL™ Mueller Hinton II Broth, cation-adjusted, sterilized by autoclaving (BD Diagnostics, cat #212322, lot #5257869, expiration May 31, 2019)
Mueller Hinton Broth 2, cation-adjusted, sterilized by autoclaving (Sigma-Aldrich, cat #90922, lot # BCBR3303V, expiration November 2020)
BBL™ Mueller Hinton II Broth, Cation-Adjusted, 400 ml, sterile (BD Diagnostics, cat #297963, lot #6014547, expiration Jan. 12, 2017)
Mueller Hinton II Broth, Cation-Adjusted, 1000 mL, sterile (Teknova, cat # M5860, lot #M586012B1601, expiration Dec. 9, 2016)
Trypticase™ Soy Agar Plates, with 5% Sheep Blood (TSA II) (BD Diagnostics, cat #221239, lot #6049996, expiration Jun. 10, 2016)

Animal and Human Blood Products
Horse Serum, donor herd, sterile filtered (Sigma-Aldrich, Cat # H1270, Lot #15G382, expiration June 2016, store frozen at −20° C.)
Horse Serum, sterile filtered (BioreclamationIVT, cat # HSESRM, lot # HSE1225, exp. October 2016, store frozen at −20° C.)
Horse Serum, New Zealand origin, donor herd, sterile filtered (Gibco, Cat #16050-122, Lot #1671315, expiration February 2019, store frozen at −20° C.)
Donor Horse Serum, U.S. Sourced, sterile filtered (Corning, Cat #35-030-CV, Lot #35030105, expiration July 2018, store frozen at −20° C.)
Donor Horse Serum, U.S. Sourced, sterile filtered (Sigma-Aldrich, cat #12449C, lot #14A277, Feb. 28, 2018, store frozen at −20° C.)
Human Serum from human male AB plasma, U.S. origin, sterile-filtered (Sigma-Aldrich, cat # SLBN4664V, expiration April 2018, store frozen at −20° C.)
Pooled Normal Human Male AB Serum, sterile filtered (Innovative Research Inc., cat # IPLA-SERAB, lot #19799, stored frozen at −20° C.)
Pooled Normal Human Male Plasma, NA-citrate anticoagulant, sterile filtered (Innovative Research Inc., cat # IPLA-N, lot #18944, store frozen at −20° C.)
Rabbit Serum, USA origin, sterile-filtered (Sigma-Aldrich, cat # R7136, Lot #13E108, expiration May 2017, store frozen at −20°
Innovative Grade US Origin Beagle Serum (Innovative Research Inc., cat # IBG-SER, Lot #17654, exp. June 2018, store at −20° C.)
Remel™ Laked Horse Blood (Thermo Scientific, cat # R54072, stored frozen at −20° C.)

Chemical Reagents
DL-Dithiothreitol solution, 1M in $H_2O$ (Sigma-Aldrich, cat #646563-10X.5ML, lot # MKBW5575V, store unopened at 24° C.)
DL-Dithiothreitol BioUltra, for molecular biology, ≥99.5% (RT) (Sigma-Aldrich, cat #43815-25G, lot # BCBBD7009V, store at 2-8° C.)
DL-Dithiothreitol (G-Biosciences, cat # RC-046, lot #151106, store at 2-8° C.)
Tris(2-carboxyethyl)phosphine hydrochloride solution, 0.5 M, pH 7.0 (Sigma-Aldrich, cat #646547-10X1ML, lot # MKBW8503V, store unopened at 24° C.)
TWEEN® 80 (Sigma-Aldrich, cat # P4780-100ML, lot # MKBW2896V, store at 24° C.)
Sodium Chloride (NaCl) (Fisher BioReagents, cat # BP358-10, lot #150661, store at 24° C.)
Calcium Chloride (Fisher Bioreagents, cat # C77-212, lot #110651, store at 24° C.)
Magnesium chloride, anhydrous, ≥98% (Sigma-Aldrich, cat # M8266-100G, lot #120M0094V, store at 24° C.)
Bovine Serum Albumin, lyophilized powder, ≥96% (Sigma-Aldrich, cat # A2153, lot # SLBL5462V, store at 2-8° C.)

Supplies and Equipment
Falcon® 96-Well Cell Culture Plates, polystyrene, sterile, u-bottom, low evaporation lid (Corning, cat #351177, lot #6026023)
BBL™ Mueller Hinton Broth, 2 ml Tubes (BD Diagnostic Systems, cat #296164, lot #6054984)
DEN-1 benchtop densitometer (Grant Biosciences, cat # DEN-1, lot #050102-1111-0426)
SpectraMax M3 Multi-Mode Microplate Reader (Molecular Devices Inc.)

REFERENCES

1. Wiegand et al. 2008. Agar and broth dilution methods to determine the minimal inhibitory concentration (MIC) of antimicrobial substances. Nature Protocols. 3:163-175.
2. Gilmer et al. 2013. Novel Bacteriophage Lysin with Broad Lytic Activity Protects against Mixed Infection by *Streptococcus pyogenes* and Methicillin-Resistant *Staphylococcus aureus*. Antimicrobial Agents and Chemotherapy. 57:2743-2750.
3. Schuch et al. 2014. Combination Therapy With Lysin CF-301 and Antibiotic Is Superior to Antibiotic Alone for Treating Methicillin-Resistant *Staphylococcus aureus*-Induced Murine Bacteremia. The Journal of Infectious Diseases. 209:1469-78.
4. Hatful G. 2015. Dark Matter of the Biosphere: the Amazing World of Bacteriophage Diversity. Journal of Virology. 89:8107-10.
5. Fischetti, V. A., Nelson, D. & Schuch, R. 2006. Reinventing phage therapy: are the parts greater than the sum? Nature Biotechnology. 24:1508-11.
6. Kusuma & Kokai-Kun. 2005. Comparison of Four Methods for Determining Lysostaphin Susceptibility of Various Strains of *Staphylococcus aureus*. Antimicrobial Agents and Chemotherapy. 49:3256-63.
7. Methods for dilution antimicrobial susceptibility tests for bacteria that grow aerobically. Vol. 32 (Clinical and Laboratory Standards Institute (US), Wayne (Pa.), 2012). *Clinical Microbiology Procedures Handbook 3rd Ed.* Washington D.C., (ASM Press, 2010).
8. Fischetti, V. A. Bacteriophage lysins as effective antibacterials. *Current opinion in microbiology* 11, 393-400 (2008).
9. Fenton, M., Ross, P., McAuliffe, O., O'Mahony, J. & Coffey, A. Recombinant bacteriophage lysins as antibacterials. *Bioengineered Bugs* 1, 9-16 (2010).
10. Nelson, D., Loomis, L. & Fischetti, V. A. Prevention and elimination of upper respiratory colonization of mice by group A streptococci by using a bacteriophage lytic enzyme. *Proceedings of the National Academy of Sciences of the United States of America* 98, 4107-4112 (2001).
11. Witzenrath, M., et al. Systemic use of the endolysin Cpl-1 rescues mice with fatal pneumococcal pneumonia. *Critical care medicine* 37, 642-649 (2009).
12. Pastagia, M., et al. A novel chimeric lysin shows superiority to mupirocin for skin decolonization of methicillin-resistant and -sensitive *Staphylococcus aureus* strains. *Antimicrobial agents and chemotherapy* 55, 738-744 (2011).
13. Loeffler, J. M., Djurkovic, S. & Fischetti, V. A. Phage Lytic Enzyme Cpl-1 as a Novel Antimicrobial for Pneumococcal Bacteremia. *Infection and Immunity* 71, 6199-6204 (2003).
14. Entenza, J. M., Loeffler, J. M., Grandgirard, D., Fischetti, V. A. & Moreillon, P. Therapeutic effects of bacteriophage Cpl-1 lysin against *Streptococcus pneumoniae* endocarditis in rats. *Antimicrobial agents and chemotherapy* 49, 4789-4792 (2005).
15. Grandgirard, D., Loeffler, J. M., Fischetti, V. A. & Leib, S. L. Phage lytic enzyme Cpl-1 for antibacterial therapy in experimental pneumococcal meningitis. *The Journal of infectious diseases* 197, 1519-1522 (2008).
16. Schuch, R., Fischetti, V. A. & Nelson, D. C. A Genetic Screen to Identify Bacteriophage Lysins. in *Bacteriophages: Methods and Protocols, Volume 2: Molecular and Applied Aspects*, Vol. 502 307-319 (2009).
17. Bateman, A. & Rawlings, N. D. The CHAP domain: a large family of amidases including GSP amidase and peptidoglycan hydrolases. *Trends Biochem Sci* 28, 234-237 (2003)
18. Whisstock, J. C. & Lesk, A. M. SH3 domains in prokaryotes. *Trends in Biochemical Sciences* 24, 132-133 (1999).
19. Rossi, P., et al. Structural elucidation of the Cys-His-Glu-Asn proteolytic relay in the secreted CHAP domain enzyme from the human pathogen *Staphylococcus saprophyticus*. *Proteins* 74, 515-519 (2009).
20. Mueller, M., de la Pena, A. & Derendorf, H. Issues in Pharmacokinetics and Pharmacodynamics of Anti-Infective Agents: Kill Curves versus MIC. *Antimicrobial agents and chemotherapy* 48, 369-377 (2004).
21. Cottarel, G. & Wierzbowski, J. Combination drugs, an emerging option for antibacterial therapy. *Trends in biotechnology* 25, 547-555 (2007).
22. Tallarida, R. J. Revisiting the isobole and related quantitative methods for assessing drug synergism. *The Journal of pharmacology and experimental therapeutics* 342, 2-8 (2012).
23. LaPlante, K. L., Leonard, S. N., Andes, D. R., Craig, W. A. & Rybak, M. J. Activities of clindamycin, daptomycin, doxycycline, linezolid, trimethoprim-sulfamethoxazole, and vancomycin against community-associated methicillin-resistant *Staphylococcus aureus* with inducible clindamycin resistance in murine thigh infection and in vitro pharmacodynamic models. *Antimicrobial agents and chemotherapy* 52, 2156-2162 (2008).
24. Crandon, J. L., Kuti, J. L. & Nicolau, D. P. Comparative efficacies of human simulated exposures of telavancin and vancomycin against methicillin-resistant *Staphylococcus aureus* with a range of vancomycin MICs in a murine pneumonia model. *Antimicrobial agents and chemotherapy* 54, 5115-5119 (2010).
25. Loeffler, J. M., Nelson, D. & Fischetti, V. A. Rapid killing of *Streptococcus pneumoniae* with a bacteriophage cell wall hydrolase. *Science* 294, 2170-2172 (2001).
26. Schuch, R., Nelson, D. & Fischetti, V. A bacteriolytic agent that detects and kills *Bacillus anthracis*. *Nature* 418, 884-889 (2002).
27. Manoharadas, S., Witte, A. & Blasi, U. Antimicrobial activity of a chimeric enzybiotic towards *Staphylococcus aureus*. *Journal of biotechnology* 139, 118-123 (2009).
28. Rashel, M., et al. Efficient elimination of multidrug-resistant *Staphylococcus aureus* by cloned lysin derived from bacteriophage phi MR11. *The Journal of infectious diseases* 196, 1237-1247 (2007).
29. Daniel, A., et al. Synergism between a novel chimeric lysin and oxacillin protects against infection by methicillin-resistant *Staphylococcus aureus*. *Antimicrobial agents and chemotherapy* 54, 1603-1612 (2010).
30. Kokai-Kun, J. F., Chanturiya, T. & Mond, J. J. Lysostaphin as a treatment for systemic *Staphylococcus aureus* infection in a mouse model. *The Journal of antimicrobial chemotherapy* 60, 1051-1059 (2007).
31. Sopirala, M. M., et al. Synergy testing by Etest, microdilution checkerboard, and time-kill methods for pan-drug-resistant *Acinetobacter baumannii*. *Antimicrobial agents and chemotherapy* 54, 4678-4683 (2010).
32. Zhang, Y. I-TASSER server for protein 3D structure prediction. *BMC bioinformatics* 9, 40 (2008).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for broth microdilution (BMD) susceptibility testing of gram-positive bacteria having human serum-like levels of activity, the method comprising evaluating an antibacterial peptide in broth supplemented with animal serum and a reducing agent, wherein the antibacterial peptide comprises a lysin polypeptide, and wherein the animal serum comprises horse serum at a concentration between 15% and 30%.

2. The method of claim h wherein the broth is supplemented with the animal horse serum at a concentration between 20% and 30%.

3. The method of claim h wherein the broth is cation-adjusted broth.

4. The method of claim h wherein the broth is Mueller Hinton Broth (MHB).

5. The method of claim h wherein the reducing agent is selected from Dithiothreitol (DTT) and Tris(2-carboxyethyl) phosphine hydrochloride (TCEP).

6. The method of claim h wherein the amount of reducing agent is between 0.1 and 1 mM.

7. The method of claim h wherein the amount of reducing agent is between 0.25 and 1 mM.

8. The method of claim 1 wherein the lysin polypeptide is PlySs2 (CF-301) or a variant or derivative thereof effective to kill gram positive bacteria.

9. The method of claim 1 for evaluating a composition comprising an antibacterial peptide which is a lysin polypeptide and further comprising one or more antibacterial agent.

10. The method of claim 9, wherein the one or more antibacterial agent is an antibiotic.

11. A method for broth microdilution (BMD) susceptibility testing of gram-positive bacteria having human serum-like levels of activity, the method comprising:
supplementing a broth with horse serum and a reducing agent to prepare a modified broth, wherein the animal serum is supplemented at a concentration of from about 15% to 40%;
contacting an antibacterial peptide with the modified broth, wherein the antibacterial peptide is a lysin polypeptide;
adding a gram-positive bacteria to the modified broth; and
determining a minimum inhibitory concentration of the antibacterial peptide.

12. The method of claim 1, wherein the reducing agent is supplemented at a concentration of from about 0.5 mM to about 1 mM.

13. The method of claim 11, wherein the reducing agent comprises one or more of Dithiothreitol (DTT), Tris(2-carboxyethyl)phosphine hydrochloride (TCEP), or combinations thereof.

14. The method of claim 11, wherein the antibacterial peptide was frozen prior to contacting with the modified broth.

15. The method of claim 14, wherein the antibacterial peptide was frozen for at least 365 days prior to contacting with the modified broth.

16. The method of claim 11, wherein the broth is a Mueller Hinton Broth.

* * * * *

UNITED STATES PATENT AND TRADEMARK OFFICE
CERTIFICATE OF CORRECTION

PATENT NO. : 10,851,401 B2
APPLICATION NO. : 16/096746
DATED : December 1, 2020
INVENTOR(S) : Raymond Schuch Page 1 of 1

It is certified that error appears in the above-identified patent and that said Letters Patent is hereby corrected as shown below:

In the Claims

In Claim 2, Column 29, Line 47, "The method of claim h" should read -- The method of claim 1 --;
In Claim 3, Column 29, Line 50, "The method of claim h" should read -- The method of claim 1 --;
In Claim 4, Column 29, Line 52, "The method of claim h" should read -- The method of claim 1 --;
In Claim 5, Column 29, Line 54, "The method of claim h" should read -- The method of claim 1 --;
In Claim 6, Column 29, Line 57, "The method of claim h" should read -- The method of claim 1 --;
In Claim 7, Column 29, Line 59, "The method of claim h" should read -- The method of claim 1 --; and
In Claim 12, Column 30, Line 52, "The method of claim 1" should read -- The method of claim 11 --.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 2

<210> SEQ ID NO 1
<211> LENGTH: 245
<212> TYPE: PRT
<213> ORGANISM: Streptococcus suis

<400> SEQUENCE: 1

```
Met Thr Thr Val Asn Glu Ala Leu Asn Asn Val Arg Ala Gln Val Gly
 1               5                  10                  15

Ser Gly Val Ser Val Gly Asn Gly Glu Cys Tyr Ala Leu Ala Ser Trp
             20                  25                  30

Tyr Glu Arg Met Ile Ser Pro Asp Ala Thr Val Gly Leu Gly Ala Gly
         35                  40                  45

Val Gly Trp Val Ser Gly Ala Ile Gly Asp Thr Ile Ser Ala Lys Asn
     50                  55                  60

Ile Gly Ser Ser Tyr Asn Trp Gln Ala Asn Gly Trp Thr Val Ser Thr
 65                  70                  75                  80

Ser Gly Pro Phe Lys Ala Gly Gln Ile Val Thr Leu Gly Ala Thr Pro
                 85                  90                  95

Gly Asn Pro Tyr Gly His Val Val Ile Val Glu Ala Val Asp Gly Asp
            100                 105                 110

Arg Leu Thr Ile Leu Glu Gln Asn Tyr Gly Gly Lys Arg Tyr Pro Val
        115                 120                 125

Arg Asn Tyr Tyr Ser Ala Ala Ser Tyr Arg Gln Gln Val Val His Tyr
    130                 135                 140

Ile Thr Pro Pro Gly Thr Val Ala Gln Ser Ala Pro Asn Leu Ala Gly
145                 150                 155                 160

Ser Arg Ser Tyr Arg Glu Thr Gly Thr Met Thr Val Thr Val Asp Ala
                165                 170                 175

Leu Asn Val Arg Arg Ala Pro Asn Thr Ser Gly Glu Ile Val Ala Val
            180                 185                 190

Tyr Lys Arg Gly Glu Ser Phe Asp Tyr Asp Thr Val Ile Ile Asp Val
        195                 200                 205

Asn Gly Tyr Val Trp Val Ser Tyr Ile Gly Gly Ser Gly Lys Arg Asn
    210                 215                 220

Tyr Val Ala Thr Gly Ala Thr Lys Asp Gly Lys Arg Phe Gly Asn Ala
225                 230                 235                 240

Trp Gly Thr Phe Lys
                245
```

<210> SEQ ID NO 2
<211> LENGTH: 280
<212> TYPE: PRT
<213> ORGANISM: Staphylococcus aureus

<400> SEQUENCE: 2

```
Met Glu Thr Leu Lys Gln Ala Glu Ser Tyr Ile Lys Ser Lys Val Asn
 1               5                  10                  15

Thr Gly Thr Asp Phe Asp Gly Leu Tyr Gly Tyr Gln Cys Met Asp Leu
             20                  25                  30

Ala Val Asp Tyr Ile Tyr His Val Thr Asp Gly Lys Ile Arg Met Trp
         35                  40                  45

Gly Asn Ala Lys Asp Ala Ile Asn Asn Ser Phe Gly Gly Thr Ala Thr
     50                  55                  60

Val Tyr Lys Asn Tyr Pro Ala Phe Arg Pro Lys Tyr Gly Asp Val Val
```

-continued

```
             65                  70                  75                  80
Val Trp Thr Thr Gly Asn Phe Ala Thr Tyr Gly His Ile Ala Ile Val
                 85                  90                  95

Thr Asn Pro Asp Pro Tyr Gly Asp Leu Gln Tyr Val Thr Val Leu Glu
                100                 105                 110

Gln Asn Trp Asn Gly Asn Gly Ile Tyr Lys Thr Glu Leu Ala Thr Ile
                115                 120                 125

Arg Thr His Asp Tyr Thr Gly Ile Thr His Phe Ile Arg Pro Asn Phe
                130                 135                 140

Ala Thr Glu Ser Ser Val Lys Lys Lys Asp Thr Lys Lys Lys Pro Lys
145                 150                 155                 160

Pro Ser Asn Arg Asp Gly Leu Asn Lys Asp Lys Ile Val Tyr Asp Arg
                165                 170                 175

Thr Asn Ile Asn Tyr Asn Met Val Leu Gln Gly Lys Ser Ala Ser Lys
                180                 185                 190

Ile Thr Val Gly Ser Lys Ala Pro Tyr Asn Leu Lys Trp Ser Lys Gly
                195                 200                 205

Ala Tyr Phe Asn Ala Lys Ile Asp Gly Leu Gly Ala Thr Ser Ala Thr
210                 215                 220

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
                245                 250                 255

Trp Cys Arg Ile Tyr Trp Asn Asn His Asn Glu Trp Ile Trp His Glu
                260                 265                 270

Arg Leu Ile Val Lys Glu Val Phe
                275                 280
```